US009079961B2

(12) United States Patent
Taniue et al.

(10) Patent No.: US 9,079,961 B2
(45) Date of Patent: Jul. 14, 2015

(54) GPIIIA GENE

(75) Inventors: Atsuko Taniue, Osaka (JP); Hiroyuki Ishii, Osaka (JP); Shinji Maekawajiri, Aki-Takata (JP); Nozomi Nagata, Aki-Takata (JP); Takanori Oka, Aki-Takata (JP)

(73) Assignees: JAPANESE RED CROSS SOCIETY, Tokyo-To (JP); WAKUNAGA PHARMACEUTICAL CO., LTD., Osaka-Fu (JP)

( * ) Notice: Subject to any disclaimer, the term of this patent is extended or adjusted under 35 U.S.C. 154(b) by 1068 days.

(21) Appl. No.: 12/451,655

(22) PCT Filed: May 26, 2008

(86) PCT No.: PCT/JP2008/059673
§ 371 (c)(1),
(2), (4) Date: Jan. 13, 2010

(87) PCT Pub. No.: WO2008/146797
PCT Pub. Date: Dec. 4, 2008

(65) Prior Publication Data
US 2010/0173292 A1 Jul. 8, 2010

(30) Foreign Application Priority Data
May 25, 2007 (JP) ................. 2007-139642

(51) Int. Cl.
*C12Q 1/68* (2006.01)
*C12P 19/34* (2006.01)
*C07H 21/02* (2006.01)
*C07H 21/04* (2006.01)
*C07K 16/28* (2006.01)
*C07K 14/705* (2006.01)
*G01N 33/86* (2006.01)

(52) U.S. Cl.
CPC ....... *C07K 16/2848* (2013.01); *C07K 14/70557* (2013.01); *C12Q 1/6883* (2013.01); *G01N 33/86* (2013.01); *C12Q 2600/156* (2013.01); *G01N 2800/222* (2013.01); *G01N 2800/245* (2013.01)

(58) Field of Classification Search
CPC ........... C07K 14/70557; C12Q 1/6883; C12Q 1/68272; G01N 2800/22
See application file for complete search history.

(56) References Cited

U.S. PATENT DOCUMENTS 6,316,196 B1 * 11/2001 Morten ........................ 435/6.14
6,582,908 B2 * 6/2003 Fodor et al. ........................ 506/9

OTHER PUBLICATIONS

Lyou et al; Transfusion, vol. 42, 2002, pp. 1089-1095.*
Kuijpers et al Blood, vol. 81, 1993, pp. 70-76.*
Ko et al; Japanese Journal of Transfusion and Cell Therapy, Apr. 2007, vol. 53, No. 2, p. 220.*
NEB catalog (1998/1999), pp. 121, 284.*
International Search Report issued Jul. 1, 2008 in International (PCT) Application No. PCT/JP2008/059673.
R. Kuijpers et al., "Single Point Mutation in Human Glycoprotein IIIa is Associated with a New Platelet-Specific Alloantigen (Mo) Involved in Neonatal Alloimmune Thrombocytopenia", Blood, vol. 81, No. 1, pp. 70-76, Jan. 1, 1993.
L. A. Fitzgerald et al., "Protein Sequence of Endothelial Glycoprotein IIIa Derived from a cDNA Clone", The Journal of Biological Chemistry, vol. 262, No. 9, pp. 3936-3939, Mar. 25, 1987.
P. Frachet et al., "GPIIb and GIIIa Amino Acid Sequences Deduced from Human Megakaryocyte cDNAs", Molecular Biology Reports, vol. 14, pp. 27-33, 1990.
Y. Ko et al., "NAITP Shorei kara Hakken Sareta Atarashii HPA-7 Idenshigata", Japanese Journal of Transfusion and Cell Therapy, vol. 53, No. 2, p. 220, Apr. 2007 in Japanese.
S. Simsek et al., "The Arg633His Substitution Responsible for the Private Platelet Antigen Gro$^a$ Unravelled by SSCP Analysis and Direct Sequencing", British Journal of Haematology, vol. 97, No. 2, pp. 330-335, 1997.
S. Simsek et al., "A New Private Platelet Antigen, Gro$^a$, Localized on Glycoprotein IIIa, Involved in Neonatal Alloimmune Thrombocytopenia", Vox Sang, vol. 67, pp. 302-306, 1994.
Supplementary European Search Report issued Mar. 23, 2011 in European Application No. 08 76 4706.
Y. Koh et al., "Neonatal Alloimmune Thrombocytopenia Caused by an Antibody Specific for a Newly Identified Allele of Human Platelet Antigen-7", Transfusion, vol. 50, No. 6, pp. 1276-1284, Jun. 2010.
Y. Fukumori et al., "Neonatal Alloimmune Thrombocytopenia (NAIT) Caused by Antibody Specific for a Newly Identified Allele of Human Platelet Antigen (HPA)-7", International Society of Blood Transfusion, vol. 97, No. Suppl. 1, p. 24, Nov. 2009.
Y. Ko et al., "NAITP Shorei kara Hakken Sareta Atarashii HPA-7 Idenshigata", Japanese Journal of Transfusion and Cell Therapy, vol. 53, No. 2, p. 220, Apr. 2007 in Japanese (along with English translation).

* cited by examiner

*Primary Examiner* — Jehanne Sitton
(74) *Attorney, Agent, or Firm* — Wenderoth, Lind & Ponack, L.L.P.

(57) ABSTRACT

An object of the present invention is to provide a probe, primer, primer set and antibody for determining neonatal alloimmune thrombocytopenic purpura or the risk of developing it. According to the present invention, there is provided a probe, primer, primer set and antibody for use in the detection of the thymine residue at position 1297 in the GPIIIa.

13 Claims, 2 Drawing Sheets

|  | 381 |  |  |  |  |  |  |  | 390 |  |  |  |  |  |  |  |  | 400 |  |  |  |  |  | 407 |  | 410 |
|---|---|---|---|---|---|---|---|---|---|---|---|---|---|---|---|---|---|---|---|---|---|---|---|---|---|---|
| HPA-7a | Trp | Ala | Gln | Leu | Cys | Leu | Asn | Thr | Ile | Phe | Leu | Ser | Ile | Gln | Val | Ser | Phe | Ser | Ile | Glu | Ala | Lys | Val | Arg | Gly | Cys | Gln | Glu | Lys |
| HPA-7b | Trp | Ala | Gln | Leu | Cys | Leu | Asn | Thr | Ile | Phe | Leu | Ser | Ile | Gln | Val | Ser | Phe | Ser | Ile | Glu | Ala | Lys | Val | Arg | Gly | Cys | Ala | Glu | Lys |
| HPA-7new | Trp | Ala | Gln | Leu | Cys | Leu | Asn | Thr | Ile | Phe | Leu | Ser | Ile | Gln | Val | Ser | Phe | Ser | Ile | Glu | Ala | Lys | Val | Arg | Gly | Cys | Ser | Glu | Lys |

|  | 411 |  |  |  |  |  |  |  |  | 420 |  |  |  |  |  |  |  |  | 430 |  |  |  |  |  |  |  |  |  | 440 |
|---|---|---|---|---|---|---|---|---|---|---|---|---|---|---|---|---|---|---|---|---|---|---|---|---|---|---|---|---|---|
| HPA-7a | Glu | Lys | Ser | Phe | Thr | Ile | Lys | Pro | Val | Gly | Phe | Lys | Asp | Ser | Leu | Ile | Val | Gln | Val | Thr | Phe | Asp | Cys | Asp | Cys | Ala | Cys | Gln | Ala | Gln |
| HPA-7b | Glu | Lys | Ser | Phe | Thr | Ile | Lys | Pro | Val | Gly | Phe | Lys | Asp | Ser | Leu | Ile | Val | Gln | Val | Thr | Phe | Asp | Cys | Asp | Cys | Ala | Cys | Gln | Ala | Gln |
| HPA-7new | Glu | Lys | Ser | Phe | Thr | Ile | Lys | Pro | Val | Gly | Phe | Lys | Asp | Ser | Leu | Ile | Val | Gln | Val | Thr | Phe | Asp | Cys | Asp | Cys | Ala | Cys | Gln | Ala | Gln |

|  | 441 |  |  |  |  |  |  |  |  | 450 |
|---|---|---|---|---|---|---|---|---|---|---|
| HPA-7a | Ala | Glu | Pro | Asn | Ser | His | Arg | Cys | Asn | Asn |
| HPA-7b | Ala | Glu | Pro | Asn | Ser | His | Arg | Cys | Asn | Asn |
| HPA-7new | Ala | Glu | Pro | Asn | Ser | His | Arg | Cys | Asn | Asn |

GPIIIA GENE

This application is a U.S. national stage of International Application No. PCT/JP2008/059673 filed May 26, 2008.

TECHNICAL FIELD

The present invention relates to a novel GPIIIa gene which is a marker for determining neonatal alloimmune thrombocytopenic purpura or the risk of developing it. More particularly, the present invention relates to a means for detecting mutation in the GPIIIa gene, a detection method and a detection kit for the mutation.

BACKGROUND ART

Platelets adhere to a site of angiopathy and are then bound (aggregated) with each other to form a thrombus, and these functions are controlled by various proteins existing on the platelet membrane. Known examples of such membrane proteins include GPI (Glycoprotein I), GPIIb (Glycoprotein IIb) and GPIIIa (Glycoprotein IIIa). With regard to GPIIIa, the full length cDNA encoding a GPIIIa protein was isolated from platelets of a normal individual, and its gene structure was specified (J. Biol. Chem. 262(9) p. 3936-3939). Further, researches on platelet antigens existing on these membrane proteins (HPA-1 to 7) have been carried out (J. Clin. Invest 40 p 1597 (1961), Prog. Hematol. 4 p 222 (1964), Vox Sang 4 p 161 (1959), Vox Sang 39 p 113 (1980)).

Platelet antigens are known as causes of neonatal alloimmune thrombocytopenic purpura (NAITP), post-transfusion purpura, refractoriness to platelet transfusion therapy, and the like. In Japanese individuals, it is said that anti-HPA-2b antibodies are involved in refractoriness to platelet transfusion therapy and anti-HPA-4-b antibodies are involved in NAITP. Thus, typing of the platelet antigen type is becoming clinically important.

Platelet antigen types occur due to polymorphisms of several glycoproteins (Table 1), which polymorphisms are yielded by a single amino acid substitution at the protein level or a single base substitution at the genetic level. Therefore, in typing of the platelet antigen based on the gene, such a difference in a single base is assessed (Japanese Journal of Transfusion Medicine. Vol. No. 1 39(1):204-211, 1993).

TABLE 1

| Antigen system | Antigen | Platelet membrane protein | Amino acid substitution | Codon |
| --- | --- | --- | --- | --- |
| HPA-1 | HPA-1a | GPIIIa | Leu (33) | CTG |
|  | HPA-1b |  | Pro | CCG |
| HPA-2 | HPA-2a | GPIb | Thu (145) | ACG |
|  | HPA-2b |  | Met | ATG |
| HPA-3 | HPA-3a | GPIIb | Ile (843) | ATC |
|  | HPA-3b |  | Ser | AGC |
| HPA-4 | HPA-4a | GPIIIa | Arg (143) | CGA |
|  | HPA-4b |  | Gln | CAA |
| HPA-5 | HPA-5a | GPIa | Glu (505) | GAG |
|  | HPA-5b |  | Lys | AAG |
| HPA-6 | HPA-6a | GPIIIa | Arg (489) | CGA, CGG |
|  | HPA-6b |  | Gln | CAG |
| HPA-7 | HPA-7a | GPIIIa | Pro (407) | CCC |
|  | HPA-7b |  | Ala | GCC |
| HPA-8 | HPA-8a | GPIIIa | Arg (636) | CGT |
|  | HPA-8b |  | Cys | TGT |
| Nak$^a$ | Nak$^{a+}$ | CD36 | Pro (90) | CCT |
|  | Nak$^{a-}$ |  | Ser | TCT |

However, unknown platelet antigen types also exist, and sufficient elucidation thereof has not been achieved yet. With regard to HPA-7, the only polymorphisms reported so far are HPA-7a wherein the base at position 1297 in the GPIIIa gene is cytosine (the amino acid at position 407 is proline) and HPA-7b wherein the base at position 1297 in the gene is guanine (the amino acid at position 407 is alanine) (Blood: 83:70-76, 1993).

SUMMARY OF THE INVENTION

The present inventors have found a novel platelet-specific antigen in an analysis of neonatal alloimmune thrombocytopenic purpura (NAITP). Specifically, the present inventors have found that the nucleotide residue at position 1297 existing in the exon 9 of the GPIIIa gene, which is normally cytosine, is substituted from cytosine to thymine in a patient suffering from neonatal alloimmune thrombocytopenic purpura. Further, the present inventors have found that this substitution was involved in neonatal alloimmune thrombocytopenic purpura (Example 1). The present invention is based on this finding.

An object of the present invention is to provide a novel mutated GPIIIa gene and protein, means for detecting mutation in the gene and the protein, a detection method and a detection kit for the mutation.

According to the present invention, there is provided a polynucleotide comprising the nucleotide sequence of the GPIIIa gene, wherein the nucleotide residue at position 1297 of the GPIIIa gene is a thymine residue; or a fragment thereof comprising the thymine residue (hereinafter referred to as the "polynucleotide according to the present invention").

According to the present invention, there is provided a protein comprising the amino acid sequence of GPIIIa protein, wherein the amino acid residue at position 407 of the GPIIIa protein is serine residue, or a fragment thereof comprising the serine residue (hereinafter referred to as the "protein according to the present invention").

According to the present invention, there is provided a primer which can hybridize with a nucleotide sequence of the polynucleotide according to the present invention or a complementary sequence thereof, and which is used for amplification, by a nucleic acid amplification method, of a region comprising the nucleotide residue at position 1297 of the GPIIIa gene or the residue pairing therewith (hereinafter referred to as the "primer according to the present invention").

According to the present invention, there is provided a primer set consisting of two or more kinds of the primers according to the present invention, which is used for amplification, by a nucleic acid amplification method, of a region comprising the nucleotide residue at position 1297 of the GPIIIa gene or the residue pairing therewith (hereinafter referred to as the "primer set according to the present invention").

According to the present invention, there is provided a probe which can hybridize with a nucleotide sequence of the polynucleotide according to the present invention or a complementary sequence thereof, and which is used for detection of the thymine residue at position 1297 of the GPIIIa gene (hereinafter referred to as the "probe according to the present invention").

According to the present invention, there is provided an antibody against the protein or a fragment thereof according to the present invention (hereinafter referred to as the "antibody according to the present invention").

According to the present invention, there is provided a method for determining neonatal alloimmune thrombocytopenic purpura or the risk of developing it, by detecting mutation in the GPIIIa gene, which comprises the step of detecting the thymine residue at position 1297 of the GPIIIa gene using the primer, the primer set or the probe according to the present invention.

Further, according to the present invention, there is provided a method for determining neonatal alloimmune thrombocytopenic purpura or the risk of developing it, by detecting mutation of the GPIIIa gene, which comprises a step of detecting the serine residue at position 407 of the GPIIIa protein using the antibody according to the present invention (hereinafter, the above-described two methods are collectively referred to as the "method of the first embodiment of the present invention").

According to the present invention, there is provided a method for determining the possibility of onset of refractoriness to platelet transfusion therapy in platelet transfusion, by detecting mutation of the GPIIIa gene, which comprises the step of detecting the thymine residue at position 1297 of the GPIIIa gene using the primer, the primer set or the probe according to the present invention.

Further, according to the present invention, there is provided a method for determining the possibility of onset of refractoriness to platelet transfusion therapy in platelet transfusion by detecting mutation of the GPIIIa gene, which comprises the step of detecting the serine residue at position 407 of the GPIIIa protein using the antibody according to the present invention (hereinafter, the above-described two methods are collectively referred to as the "method of the second embodiment of the present invention").

According to the present invention, there is provided a kit for determining neonatal alloimmune thrombocytopenic purpura or the risk of developing it, comprising at least the primer, the primer set, the probe or the antibody according to the present invention.

According to the present invention, there is provided a kit for determining the possibility of onset of refractoriness to platelet transfusion therapy in platelet transfusion, comprising at least the primer, the primer set, the probe or the antibody according to the present invention.

The probe, the primer, the primer set or the antibody according to the present invention can be used as a marker for determining neonatal alloimmune thrombocytopenic purpura or the risk of developing it. Therefore, the present invention is useful for genetic testing for neonatal alloimmune thrombocytopenic purpura and the like. Further, the probe, the primer, the primer set or the antibody according to the present invention can be used as a marker for determining the possibility of onset of refractoriness to platelet transfusion therapy in platelet transfusion. Therefore, the present invention is useful for prediction of the effect of transfusion in platelet transfusion and the like.

BRIEF DESCRIPTION OF THE DRAWINGS

FIG. 1 sets forth sequences of GPIIIa gene and the novel GPIIIa gene. HPA-7a indicates the HPA-7a gene (SEQ ID NO: 19), HPA-7b indicates the HPA-7b gene (SEQ ID NO: 20), and HPA-7new (SEQ ID NO: 21) indicates a novel gene different from the HPA-7a gene and the HPA-7b gene.

FIG. 2 sets forth the amino acid sequences of the GPIIIa protein and the novel GPIIIa protein. HPA-7a indicates the HPA-7a protein (SEQ ID NO: 22), HPA-7b indicates the HPA-7b protein (SEQ ID NO: 23), and HPA-7new (SEQ ID NO: 24) indicates a novel gene different from the HPA-7a protein and the HPA-7b protein.

DETAILED DESCRIPTION OF THE INVENTION

[Mutated Gene and Mutated Protein]

The polynucleotide according to the present invention can be used as a labeled standard nucleic acid in competitive hybridization for detecting the mutation of the nucleotide residue at position 1297 of the GPIIIa gene, that is, substitution to the thymine residue (hereinafter, referred to as the "1297T polymorphism of the GPIIIa gene") (Example 1). Further, it can be used as a nucleotide sequence of an oligonucleotide probe for use in the detection.

In the present specification, the "nucleotide residue at position 1297 of the GPIIIa gene" means the nucleotide residue located at the 1297th position counted from the starting point, that is, the 1st residue which is the adenine residue of the initiation codon in the region encoding a signal peptide in the GPIIIa gene.

At positions 1 to 78 of the GPIIIa gene constitute the region encoding a signal peptide, and at positions 79 to 2364 of the GPIIIa gene constitute the region encoding a mature protein.

The labeled standard nucleic acid for detecting the 1297T polymorphism of the GPIIIa gene may be one capable of detecting the substitution of the nucleotide residue at position 1297 of the GPIIIa gene to the thymine residue, and may also be a fragment of the polynucleotide according to the present invention. The fragment of the polynucleotide according to the present invention is, in particular, a fragment of a polynucleotide comprising a nucleotide sequence of the GPIIIa gene of which the nucleotide residue at position 1297 is a thymine residue, wherein the fragment comprises the thymine residue.

The polynucleotide according to the present invention includes a polynucleotide selected from the following (i), (ii), (iii) and (iv):

(i) a polynucleotide comprising the nucleotide sequence of SEQ ID NO: 1;

(ii) a polynucleotide which consists a nucleotide sequence of SEQ ID NO: 1 in which one or more nucleotides are inserted, substituted and/or deleted and/or one or more nucleotides are added to one or both of its ends, and which encodes a protein functionally equivalent to a protein consisting of the amino acid sequence of SEQ ID NO: 2 (with the proviso that, in the polynucleotide, the nucleotide residue at position 1297 of the nucleotide sequence of SEQ ID NO: 1 is a thymine residue);

(iii) a polynucleotide which hybridizes, under stringent conditions, with a polynucleotide consisting of the complementary sequence of the nucleotide sequence of SEQ ID NO: 1, and which encodes a protein functionally equivalent to a protein consisting of the amino acid sequence of SEQ ID NO: 2 (with the proviso that, in the polynucleotide, the nucleotide residue corresponding to the nucleotide residue at position 1297 of the nucleotide sequence of SEQ ID NO: 1 a thymine residue); and (iv) a polynucleotide which has 70% or more identity with a polynucleotide consisting of the nucleotide sequence of SEQ ID NO: 1, and which encodes a protein functionally equivalent to a protein consisting of the amino acid sequence of SEQ ID NO: 2 (with the proviso that, in the polynucleotide, the nucleotide residue corresponding to the nucleotide residue at position 1297 of the nucleotide sequence of SEQ ID NO: 1 is a thymine residue).

The sequence as positions 1 to 78 of the nucleotide sequence of SEQ ID NO: 1 is a sequence encoding a signal peptide (GenBank Accession No. NM_000212). In the present invention, the sequence encoding a signal peptide is not limited to this sequence as long as it can encode a peptide capable of functioning as a signal peptide.

The polynucleotide according to the present invention is preferably a polynucleotide encoding a protein consisting of the amino acid sequence of SEQ ID NO: 2 or a part thereof comprising the amino acid residue at position 407 of the amino acid sequence of SEQ ID NO: 2.

In the present invention, when the amino acid sequence of the SEQ ID NO: 2 is given, nucleotide sequences encoding it can be easily determined, and various nucleotide sequences encoding the amino acid sequence of SEQ ID NO: 2 can be selected.

Accordingly, a polynucleotide encoding a protein consisting of the amino acid sequence of SEQ ID NO: 2 also means not only a part of or the entire DNA sequence of SEQ ID NO: 1, a DNA sequence encoding the same amino acids, which has a codon having a degeneratcy relationship therewith as a DNA sequence. The present invention further includes RNA sequences corresponding to these sequences.

A Preferred example of a polynucleotide encoding a protein consisting of the amino acid sequence of SEQ ID NO: 2 includes a polynucleotide consisting of a nucleotide sequence of SEQ ID NO: 1.

In the present specification, whether or not a protein is functionally equivalent to the protein consisting of the amino acid sequence of SEQ ID NO: 2 can be determined by assessing biological phenomena or functions related to the expression of the protein consisting of the amino acid sequence of SEQ ID NO: 2.

The polynucleotide according to the present invention is preferably a polynucleotide consisting of the nucleotide sequence of SEQ ID NO: 1 or a fragment thereof comprising the nucleotide residue at position 1297 of SEQ ID NO: 1. The polynucleotide according to the present invention is more preferably a polynucleotide comprising at least a polynucleotide consisting of the nucleotide sequence of SEQ ID NO: 7 (nucleotide sequence at positions 1201 to 1391 in SEQ ID NO: 1). The polynucleotide according to the present invention is still more preferably a polynucleotide comprising at least a polynucleotide consisting of the nucleotide sequence of SEQ ID NO: 3 (nucleotide sequence at positions 1281 to 1320 in SEQ ID NO: 1).

The protein according to the present invention can be used as an antigen for preparation of an antibody capable of detecting the mutation of the amino acid residue at position 407 of the GPIIIa protein, that is, the substitution to the serine residue (hereinafter, referred to as the "407S polymorphism of the GPIIIa protein).

In the present specification, the "amino acid residue at position 407 of the GPIIIa protein" means the amino acid residue located at the 407th position counted from the starting point, that is, the 1st residue, which is the glycine residue at the N-terminus of the amino acid sequence constituting the mature GPIIIa protein.

The "mature GPIIIa protein" indicates a protein encoded by the nucleotide sequence at positions 79 to 2364 of the GPIIIa gene, which does not comprise the signal peptide. For example, it is a protein consisting of the amino acid sequence of SEQ ID NO: 6.

The protein according to the present invention includes a protein selected from the following (v), (vi), (vii) and (viii):

(v) a protein comprising the amino acid sequence of SEQ ID NO: 2;

(vi) a protein which consists an amino acid sequence of SEQ ID NO: 2 in which one or more amino acids are inserted, substituted and/or deleted and/or one or more amino acids are added to one or both of its ends, and which is functionally equivalent to a protein consisting of the amino acid sequence of SEQ ID NO: 2 (with the proviso that the amino acid residue at position 407 of the amino acid sequence of SEQ ID NO: 2 is a serine residue);

(vii) a protein which is encoded by a polynucleotide hybridizing, under stringent conditions, with a polynucleotide consisting of the complementary sequence of the nucleotide sequence of a polynucleotide encoding the amino acid sequence of SEQ ID NO: 2, and which is functionally equivalent to a protein consisting of the amino acid sequence of SEQ ID NO: 2 (with the proviso that the amino acid residue corresponding to the amino acid residue at position 407 of the amino acid sequence of SEQ ID NO: 2 is a serine residue); and (viii) a protein which consists of an amino acid sequence having 70% or more identity with the amino acid sequence of SEQ ID NO: 2, and which is functionally equivalent to a protein consisting of the amino acid sequence of SEQ ID NO: 2 (with the proviso that the amino acid residue corresponding to the amino acid residue at position 407 of the amino acid sequence of SEQ ID NO: 2 is a serine residue).

The protein according to the present invention is preferably a protein consisting of the amino acid sequence of SEQ ID NO: 2 or a fragment thereof comprising the amino acid residue at position 407 of SEQ ID NO: 2. The protein according to the present invention is more preferably a protein (polypeptide) comprising at least a polypeptide consisting of the amino acid sequence of SEQ ID NO: 8 (amino acid sequence at positions 381 to 450 in SEQ ID NO: 2). The protein according to the present invention is still more preferably a protein (polypeptide) comprising at least a polypeptide consisting of the amino acid sequence of SEQ ID NO: 4 (amino acid sequence at positions 395 to 420 in SEQ ID NO: 2).

The antigen for preparing an antibody capable of detecting the 407S polymorphism of the GPIIIa protein may be one capable of detecting the substitution of the amino acid residue at position 407 in the GPIIIa protein to the serine residue, and may also be a fragment of the protein (peptide) according to the present invention. The fragment of the protein according to the present invention is, in particular, a fragment of a protein comprising the amino acid sequence of the GPIIIa protein of which the amino acid residue at position 407 is a serine residue, wherein the fragment comprises the serine residue.

The fragment of the protein according to the present invention is a polypeptide having at least 6 amino acid residues (for example, 8, 10, 12 15 or more amino acid residues).

In the present invention, the "GPIIIa gene" is known as a gene encoding a membrane protein of platelets, and has been registered under GenBank Accession No. M35999 (SEQ ID NO: 5 (base sequence), SEQ ID NO: 6 (amino acid sequence)) or Accession No. NM_000212.

The GPIIIa gene includes not only the polynucleotide of the following (I'), but also a homologous polynucleotide selected from the following (ii'), (iii') and (iv'):

(i') a polynucleotide comprising the nucleotide sequence of SEQ ID NO: 5;

(ii') a polynucleotide which consists of a nucleotide sequence of SEQ ID NO: 5 in which one or more nucleotides are inserted, substituted and/or deleted and/or one or more nucleotides are added to one or both of its ends, and which encodes a protein functionally equivalent to a protein consisting of the amino acid sequence of SEQ ID NO: 6;

(iii') a polynucleotide which hybridizes, under stringent conditions, with a polynucleotide consisting of the complementary sequence of the nucleotide sequence of SEQ ID NO: 5, and which encodes a protein functionally equivalent to a protein consisting of the amino acid sequence of SEQ ID NO: 6; and (iv') a polynucleotide which has 70% or more identity with a polynucleotide consisting of the nucleotide sequence of SEQ ID NO: 5, and which encodes a protein functionally equivalent to a protein consisting of the amino acid sequence of SEQ ID NO: 6.

The sequence at positions 1 to 78 of the nucleotide sequence of SEQ ID NO: 5 is a sequence encoding the signal peptide (GenBank Accession No. NM_000212). In the present invention, the sequence encoding the signal peptide is not limited to this sequence as long as it can encode a peptide capable of functioning as a signal peptide.

The GPIIIa gene is preferably a polynucleotide comprising the nucleotide sequence of SEQ ID NO: 5.

Further, the GPIIIa gene is preferably a polynucleotide encoding a protein comprising the amino add sequence of SEQ ID NO: 6.

As the GPIIIa protein, in addition to the protein of (v') below, homologous proteins (polypeptides) selected from (vi'), (vii'), and (viii') are provided:

(v') a protein comprising the amino acid sequence of SEQ ID NO: 6;

(vi') a protein which consists of an amino acid sequence as of SEQ ID NO: 6 in which one or more amino acids are inserted, substituted and/or deleted and/or one or more amino acids are added to one or both of its ends, and which is functionally equivalent to a protein consisting of the amino acid sequence of SEQ ID NO: 6;

(vii') a protein which is encoded by a polynucleotide which hybridizing, under stringent conditions, with a polynucleotide consisting of the complementary sequence of a nucleotide sequence of a polynucleotide encoding the amino acid sequence of SEQ ID NO: 6, and which is functionally equivalent to a protein consisting of the amino acid sequence of SEQ ID NO: 6; and (viii') a protein which consists of an amino acid sequence having 70% or more identity with the amino acid sequence of SEQ ID NO: 6, and which is functionally equivalent to a protein consisting of the amino acid sequence of SEQ ID NO: 6.

The GPIIIa protein is preferably a protein encoded by the nucleotide sequence of SEQ ID NO: 5.

Further, as the GPIIIa protein, there is more preferably provided a protein comprising the amino acid sequence of SEQ ID NO: 6.

In the present specification, "one or more nucleotides are inserted, substituted and/or deleted, and/or one or more nucleotides are added to one or both of its ends" and "one or more amino acids are inserted, substituted and/or deleted, and/or added to one or both of its ends" mean that modification has been carried out by a well-known technical method such as site-directed mutagenesis, or by substitution of a plurality of nucleotides or amino acids to an extent that it may naturally occur. The number of nucleotides or amino acids to be modified may be, for example, 1 to 30, preferably 1 to 20, more preferably 1 to 10, still more preferably 1 to 4, especially preferably 1 to 2 insertion(s), substitution(s) or deletion(s), and/or addition(s) to one or both of the ends.

The modified nucleotide sequence of the polynucleotide according to the present invention is a modified nucleotide sequence which does not affect the nucleotide residue at position 1297 of the GPIIIa gene, and may preferably be an nucleotide sequence of the polynucleotide according to the present invention having one or more (e.g., one or several, or 1, 2, 3 or 4) mutations which do not affect functions of a protein consisting of the amino acid sequence of SEQ ID NO: 2.

The modified nucleotide sequence of the GPIIIa gene may preferably be a nucleotide sequence of the GPIIIa gene having one or more (e.g., one or several, or 1, 2, 3 or 4) mutations which do not affect functions of a protein consisting of the amino acid sequence of SEQ ID NO: 6.

The modified amino acid sequence of the protein according to the present invention is a modified amino acid sequence which does not affect the amino acid residue at position 407 of the GPIIIa protein, and may preferably be an amino acid sequence of the protein according to the present invention shown in SEQ ID NO: 2 having one or more (e.g., one or several, or 1, 2, 3 or 4) conservative substitutions.

The modified amino acid sequence of the GPIIIa protein may preferably be the amino acid sequence of the GPIIIa protein shown in SEQ ID NO: 6 having one or more (e.g., one or several, or 1, 2, 3 or 4) conservative substitutions.

In the present specification, a "conservative substitution(s)" means that one or more amino acid residues are substituted by an amino acid residue(s) which is/are chemically similar thereto such that functions of the protein is not modified substantially. Examples thereof include cases where a certain hydrophobic residue is substituted by another hydrophobic residue and cases where a certain polar residue is substituted by another polar residue having the same electric charge. Such a functionally similar amino acid(s) which can be substituted is/are known in the art for every amino acid. Particular examples thereof include, as nonpolar (hydrophobic) amino acids, alanine, valine, isoleucine, leucine, proline, tryptophan, phenylalanine and methionine. Examples of polar (neutral) amino acids include glycine, serine, threonine, tyrosine, glutamine, asparagine and cysteine. Examples of (basic) amino acids having positive charge include arginine, histidine and lysine. Examples of (acidic) amino acids having negative charge include aspartic acid and glutamic acid.

In the present specification, "hybridize" means to hybridize, under stringent conditions, with a target polynucleotide, whereas not to hybridize with nucleotides other than the target nucleotide. The "stringent condition" can be determined based on the melting temperature (° C.) of the double strand formed by the probe sequence or the primer sequence and the complementary strand thereof, the salt concentration of the solution and the like. Setting an appropriate stringent condition after selecting a probe sequence or a primer sequence is a technique well-known to those skilled in the art (for example, Molecular Cloning 2nd edition, Cold Spring Harbor Laboratory (1989)).

The hybridization can be carried out according to a known method. In cases where a commercially available library is used, it can be carried out according to the method described in the manufacturer's instruction attached thereto.

In the present specification, the term "identity" regarding a base sequence or an amino acid sequence means the degree of coincidence, between sequences to be compared, of the bases or amino acid residues constituting each sequence. The value of every "identity" indicated in the present specification may be a value calculated by a homology search program known to those skilled in the art, and can be easily calculated by FASTA, BLAST or the like using the default (initial setting) parameters.

An amino acid sequence having 70% or more identity with the amino acid sequence of SEQ ID NO: 2 may be an amino acid sequence having preferably 80% or more, more preferably 85% or more, still more preferably 90% or more, still more preferably 95% or more, still more preferably 98% or more, and most preferably 99% or more identity therewith.

An amino acid sequence having 70% or more identity with the amino acid sequence of SEQ ID NO: 6 may be an amino acid sequence having preferably 80% or more, more preferably 85% or more, still more preferably 90% or more, still more preferably 95% or more, still more preferably 98% or more, and most preferably 99% or more identity therewith.

In the present invention, when the amino acid sequence of the SEQ ID NO: 6 is given, nucleotide sequences encoding it can be easily determined, and various nucleotide sequences encoding the amino acid sequence of SEQ ID NO: 6 can be selected.

Accordingly, a polynucleotide encoding a protein comprising the amino acid sequence of SEQ ID NO: 6 also means not only a part of or the entire DNA sequence of SEQ ID NO: 5, a DNA sequence encoding the same amino acids, which has a codon having a degeneratcy relationship therewith as a DNA sequence. The present invention further, includes RNA sequences corresponding to these sequences.

A Preferred example of a polynucleotide encoding a protein comprising the amino acid sequence of SEQ ID NO: 6 includes a polynucleotide comprising the nucleotide sequence of SEQ ID NO: 5.

In the present specification, whether or not a protein is functionally equivalent to the protein consisting of the amino acid sequence of SEQ ID NO: 6 can be determined by assessing biological phenomena or functions related to the expression of the protein consisting of the amino acid sequence of SEQ ID NO: 6.

According to the present invention, there is provided a polynucleotide consisting of a complementary sequence of a nucleotide sequence of a polynucleotide comprising a nucleotide sequence of the GPIIIa gene, wherein the nucleotide residue at position 1297 of the GPIIIa gene is the thymine residue, or a fragment thereof comprising the residue pairing with the thymine residue.

[Primer and Primer Set]

The primer according to the present invention can hybridize specifically with the polynucleotide according to the present invention, to amplify, by a nucleic acid amplification method, a region comprising the nucleotide residue at position 1297 of the GPIIIa gene or the residue pairing therewith. Therefore, the primer according to the present invention can be used as a marker for determining neonatal alloimmune thrombocytopenic purpura or the risk of developing it. Further, the primer according to the present invention can be used as a marker for determining the possibility of onset of refractoriness to platelet transfusion therapy in platelet transfusion.

The primer according to the present invention means one composed of deoxyribonucleic acid (DNA), ribonucleic acid (RNA) or the like, and preferably one composed of DNA.

The primer according to the present invention may amplify, by a nucleic acid amplification method, a region comprising the nucleotide residue at position 1297 of the GPIIIa gene or the residue pairing therewith in the nucleotide sequence of the polynucleotide according to the present invention or the complementary sequence thereof. Examples thereof include those consisting of a polynucleotide having at least 10, preferably at least 15, more preferably at least 20, still more preferably at least 21 contiguous nucleotide residues in the nucleotide sequence of the polynucleotide according to the present invention or the complementary sequence thereof. Further, examples of the primer of the present invention include those consisting of a polynucleotide having 10 to 30, 12 to 30, to 30, 20 to 30, and 21 to 30 contiguous nucleotide residues in a nucleotide sequence of the polynucleotide according to the present invention or a complementary sequence thereof.

Further, the primer according to the present invention may be one capable of hybridizing with a region comprising the nucleotide residue at position 1297 of the GPIIIa gene or the residue pairing therewith, in a nucleotide sequence of the polynucleotide according to the present invention or a complementary sequence thereof.

Here, a polynucleotide comprising contiguous nucleotides in a nucleotide sequence of the polynucleotide according to the present invention or a complementary sequence thereof may function as the primer according to the present invention, and examples thereof also include a modified polynucleotide comprising contiguous nucleotides in a nucleotide sequence of the polynucleotide according to the present invention or a complementary sequence thereof in which one or several (e.g., 1, 2, 3 or 4) mutations (which may be selected, for example, from insertion, substitution, deletion and addition) are introduced, wherein the mutation does not affect the nucleotide residue at position 1297 of the GPIIIa gene. An example of a modified polynucleotide include a polynucleotide which comprises at least 12 to 30 contiguous nucleotides of the nucleotide sequence of SEQ ID NO: 1 or a complementary sequence thereof having one or several mutations introduced thereto, and which functions as the primer according to the present invention.

The length of the primer according to the present invention may be at least 10 bases, and is preferably at least 15 bases, more preferably at least 20 bases, still more preferably at least 21 bases. Further, the primer according to the present invention is 12 to 30 bases, 20 to 30 bases, or 21 to 30 bases in length.

According to a preferred embodiment of the primer according to the present invention, there is provided a primer having a length of 12 to 30 bases which consists of a polynucleotide having at least 10 (more preferably at least 15, still more preferably at least 20, still more preferably at least 21) contiguous nucleotides of a nucleotide in a nucleotide sequence of the polynucleotide according to the present invention or a complementary sequence thereof; which can amplify, by a nucleic acid amplification method, a region comprising the nucleotide residue at position 1297 of a nucleotide sequence of the GPIIIa gene, and which is for use in the detection of the 1297T polymorphism of the GPIIIa gene.

The primer according to the present invention may also be used as a primer set comprising a combination of two or more kinds of the primers according to the present invention.

The primer set according to the present invention can be selected in such a way that a region comprising the nucleotide residue at position 1297 of the GPIIIa gene or a residue pairing therewith, in a nucleotide sequence of the polynucleotide according to the present invention or a complementary sequence thereof, can be amplified by a nucleic acid amplification method. A nucleic acid amplification method is well-known, and those skilled in the art can select a pair of primers for amplification of a nucleic acid as appropriate. For example, in the PCR method, primers can be selected in such a way that one of two primers pairs with the plus strand of the GPIIIa mutated gene, the other primer pairs with the minus strand of the GPIIIa mutated gene, and with a strand extended by one primer the other primer pairs. Further, in the LAMP method (WO 00/28082), three regions from the 3'-terminus, that is, F3c, F2c and F1c, and three regions from the 5'-terminus, that is, B1, B2 and B3, are each defined for a target gene, which six regions may be used for designing four kinds of primers.

The primer and the primer set according to the present invention can be used as a primer and a primer set in a known nucleic acid amplification method such as a PCR method (Saiki, R. K., Bugawan, T. L., et al. (1986) Nature, 324, 163-166), an NASBA method (Comptom, J. (1991) Nature, 650, 91-92), a TMA method (Kacian, D. L., and Fultz, T. J. (1995) U.S. Pat. No. 5,399,491), an SDA method (Walker, G. T., Little, M. C., et al (1992) Proc. Natl. Acad. Sci. USA, 89, 392-396) or a PCR-SSCP method (Orita, M., Iwahara, H., et al. (1989) Proc. Natl. Acad. Sci. USA, 86, 2776-2770) according to a conventional method.

The primers according to the present method may be chemically synthesized based on the nucleotide sequences disclosed in the present specification. Preparation of a primer is well known, and can be carried out according to a conventional method.

[Probe]

The probe according to the present invention specifically hybridizes with the polynucleotide according to the present invention, and can detect the 1297T polymorphism of the GPIIIa gene. Therefore, the probe according to the present invention can be used as a marker for determining neonatal alloimmune thrombocytopenic purpura and/or the risk of developing it. Further, the probe according to the present invention can be used as a marker for determining the possibility of onset of refractoriness to platelet transfusion therapy in platelet transfusion.

The probe according to the present invention means one consisting of deoxyribonucleic acid (DNA), ribonucleic acid (RNA) or the like, and is preferably one consisting of DNA.

An example of the probe according to the present invention includes those capable of hybridizing with a region comprising the nucleotide residue at position 1297 of the GPIIIa gene or the residue pairing therewith, in the nucleotide sequence of the polynucleotide according to the present invention or the complementary sequence thereof.

An example of the probe according to the present invention includes those consisting of a polynucleotide comprising at least 10, preferably at least 14, more preferably at least 15, still more preferably at least 16 contiguous nucleotide residues in a nucleotide sequence of the polynucleotide according to the present invention or a complementary sequence thereof. Further, an example of the probe of the present invention includes those consisting of a polynucleotide comprising 10 to 20, 12 to 20, 14 to 20, 15 to 20, and 16 to 20, 10 to 30, 12 to 30, 14 to 30, 15 to 30 or 16 to 30 contiguous nucleotide residues in a nucleotide sequence of the polynucleotide according to the present invention or a complementary sequence thereof.

Here, the polynucleotide comprising the contiguous nucleotides in a nucleotide sequence of the polynucleotide according to the present invention or a complementary sequence thereof may function as the probe according to the present invention, and examples thereof also include a modified polynucleotide comprising the contiguous nucleotides in a nucleotide sequence of the polynucleotide according to the present invention or a complementary sequence thereof in which one or several (e.g., 1, 2, 3 or 4) mutations (which may be selected, for example, from insertion, substitution, deletion and addition) are introduced, wherein the mutation does not affect the nucleotide residue at position 1297 of the GPIIIa gene. An example of a modified polynucleotide includes a polynucleotide which comprises at least 12 to 30 contiguous nucleotides in a nucleotide sequence of SEQ ID NO: 1 or a complementary sequence thereof having 1 or several mutations introduced thereto, and which functions as the probe according to the present invention.

The length of the probe according to the present invention is at least 10 bases. Further, the length of the probe according to the present invention is 12 to 30 bases.

According to a preferred embodiment of the probe according to the present invention, there is provided a probe and a primer having a length of 12 to 30 bases, which consists of a polynucleotide having at least 10 (more preferably at least 15) contiguous nucleotides in a nucleotide sequence of the polynucleotide according to the present invention or a complementary sequence thereof, which can hybridize with a region comprising the nucleotide residue at position 1297 of a nucleotide sequence of the GPIIIa gene, and which is for use in the detection of the 1297T polymorphism of the GPIIIa gene.

The probe according to the present invention can be used as a probe in a known method such as a northern blotting method, a southern blotting method or an in situ hybridization method, according to a conventional method.

The probe according to the present invention can be chemically synthesized based on a nucleotide sequence disclosed in the present specification. Preparation of a primer is well-known, and can be carried out according to a conventional method.

[Antibody]

The antibody according to the present invention can specifically recognize the protein according to the present invention, and can detect the 407S polymorphism of the GPIIIa protein. Therefore, the antibody according to the present invention can be used as a marker for determining neonatal alloimmune thrombocytopenic purpura or the risk of developing it. Further, the antibody according to the present invention can be used as a marker for determining the possibility of onset of refractoriness to platelet transfusion therapy in platelet transfusion.

According to a preferred embodiment of the antibody according to the present invention, there is provided an antibody which recognizes a region comprising the amino acid residue at position 407 of the GPIIIa protein in an amino acid sequence of the protein according to the present invention. By using such an antibody, the 407S polymorphism of the GPIIIa protein can be detected. Examples of such an antibody include an antibody against a protein comprising at least 6 amino acid residues having the amino acid residue at position 407 in the amino acid sequence of SEQ ID NO: 2.

An example of an antibody against the protein according to the present invention includes an antibody against a protein having the amino acid sequence of SEQ ID NO: 2 or a part thereof.

An example of an antibody according to the present invention includes a polyclonal antibody, a monoclonal antibody, a chimeric antibody, a single-stranded antibody (scFv), a humanized antibody, a polyspecific antibody, and an antibody fragment such as Fab, Fab, $F(ab')_2$, Fc and Fv.

The antibody according to the present invention can be obtained using a method well-known to those skilled in the art.

[Detection Method]

The substitution of the nucleotide residue at position 1297 in the nucleotide sequence of the GPIIIa gene to the thymine residue can be an index of neonatal alloimmune thrombocytopenic purpura or the risk of developing it. Therefore, according to the present invention, neonatal alloimmune thrombocytopenic purpura or the risk of developing it can be determined by detecting the 1297T polymorphism of the GPIIIa gene.

There is a possibility that the platelet antigen (HPA-7 antigen) wherein the nucleotide residue at position 1297 in the GPIIIa gene is substituted to the thymine residue causes refractoriness to platelet transfusion therapy in platelet transfusion due to the difference in the antigen. Therefore, the substitution can be an index of whether or not refractoriness to platelet transfusion therapy occurs in platelet transfusion, that is, an index of the effect of transfusion in platelet transfusion. Thus, according to the present invention, the possibility of onset of refractoriness to platelet transfusion therapy in platelet transfusion can be determined by detecting the 1297T polymorphism of the GPIIIa gene.

The detection method according to the present invention is not limited as long as it is a method capable of detecting the 1297T polymorphism of the GPIIIa gene or the 407S polymorphism of the GPIIIa protein in a test sample, and examples thereof include a hybridization method, a nucleic acid amplification method and an antigen-antibody reaction method.

Here, the "test sample" may comprise a region containing the nucleotide residue at position 1297 of the GPIIIa gene or the amino acid residue at position 407 of the GPIIIa protein, and can be obtained by extraction of the gene, mRNA or protein from a person to be tested (subject). The mRNA can be converted to cDNA as required before use. In the present specification, the "gene" also includes such a cDNA.

Here, the "subject" may be, in addition to a newborn; a blood relative of the newborn. The present invention is advantageous in the respect that the risk of developing neonatal alloimmune thrombocytopenic purpura can be determined prenatally.

The gene, mRNA or protein of the subject can be extracted from any cells in the body, and the cells are preferably cells of leucocytes.

According to the present invention, the extracted gene or mRNA can be subjected as it is to a restriction fragment length polymorphism method (RFLP method) (Southerns, E. M. (1975) J. Mol. Biol. 98, 503), an allele-specific oligonucleotide probe method (ASO method) (Wallace, R. B., Schaffer, N. J., et al. (1979) Nucleic Acid Res., 6, 3543) or an Oligonucleotide Ligation Assay method, to detect the 1297T polymorphism of the GPIIIa gene.

According to the detection method of the present invention, the 1297T polymorphism of the GPIIIa gene in a test sample can be detected by amplification of a nucleic acid sample (mRNA or a reverse transcription product thereof) by a nucleic acid amplification method using the primer or the primer set according to the present invention and analyzing the amplification product.

The detection of the 1297T polymorphism of the GPIIIa gene using a nucleic acid amplification method can be carried out by, for example, the following steps of:

(c) performing a nucleic acid amplification method using a polynucleotide derived from a test sample as the template and the primer or the primer set according to the present invention; and (d) analyzing a formed amplification product.

In step (c), mRNA prepared from the test sample or the complementary DNA (cDNA) reverse-transcribed from the mRNA can be used as the template.

The amplification of the gene can be carried out using a nucleic acid amplification method such as a PCR method (Saiki, R. K., Bugawan, T. L., et al. (1986) Nature, 324, 163-166), an NASBA method (Comptom, J. (1991) Nature, 650, 91-92), a TMA method (Kacian, D. L., and Fultz, T. J. (1995) U.S. Pat. No. 5,399,491) or an SDA method (Walker, G. T., Little, M. C., et al (1992) Proc. Natl. Acad. Sci. USA, 89, 392-396).

A gene amplified by these methods can be used to detect the 1297T polymorphism of the GPIIIa gene depending on the characteristics of the amplification product. For example, with a fragment amplified by the PCR method, the nucleotide sequence can be easily determined by a base sequence determination method, and thereby, it can be determined whether or not the nucleotide residue at position 1297 of the GPIIIa gene is thymine.

The amplification of the gene by PCR may also be carried out using a PCR-SSCP method (Orita, M., Iwahara, H., et al. (1989) Proc. Natl. Acad. Sci. USA, 86, 2776-2770) that the difference of one base is recognized. A PCR-SSCP method is a method wherein nucleic acid fragment amplified by PCR are heat-denatured to form single strands, and separated using nondenaturing polyacrylamide gel at a constant temperature. The method can detect a difference of one base by assesing, as the difference in the electrophoretic mobility, the difference in formation of the higher-order structure due to the difference of a nucleotide fragment.

Otherwise, a fragment amplified by a PCR method can be analyzed by a restriction fragment length polymorphism method (RFLP method) (Southerns, E. M. (1975) J. Mol. Biol. 98, 503), an allele-specific oligonucleotide probe method (ASO method) (Saiki, R. K, Bugawan, T. L., et al, (1986) Nature, 324, 163-166), an Oligonucleotide Ligation Assay method (Landegren, U, Kaiser, R., et al. (1990) PCR Protocols, Academic Press, Inc. p 92-98), a PCR-PHFA method (Oka, T., Matsunaga, H., et al. (1994) Nucleic Acids Res. 22, 1541-1547), a PCR-rSSO method (Kawai, S., et al, (1994) Hum Immunol, 41(2), 121-126) or the like. In cases where multiple samples are treated simultaneously, a PCR-PHFA method or a PCR-rSSO method is preferred.

According to the detection method of the present invention, the 1297T polymorphism of the GPIIIa gene in the test sample can be detected by amplificating a nucleic acid sample (mRNA or a reverse transcription product thereof), by a nucleic acid amplification method, using the primer or the primer set according to the present invention, which can hybridize with a region comprising the nucleotide residue at position 1297 of the GPIIIa gene or the residue pairing therewith in a nucleotide sequence of the polynucleotide according to the present invention or a complementary sequence thereof, and detecting the amplification product.

According to the first embodiment of the method according to the present invention, the subject for which the nucleotide residue at position 1297 is identified as thymine is given the assessment that the 1297T polymorphism of the GPIIIa gene is detected, and therefore can be diagnosed or determined to be a patient with neonatal alloimmune thrombocytopenic purpura or to have the risk of developing it.

According to the second embodiment of the method according to the present invention, the subject for which the nucleotide residue at position 1297 is identified as thymine is given the assessment that the 1297T polymorphism of the GPIIIa gene is detected, and therefore can be diagnosed or determined to have a possibility of developing refractoriness to platelet transfusion therapy in platelet transfusion.

According to the detection method of the present invention, the 1297T polymorphism of the GPIIIa gene in a test sample can be detected by hybridizing the probe according to the present invention with a nucleic acid sample (mRNA or a reverse transcription product thereof) and detecting the hybridization complex, that is, a double-stranded nucleotides.

For a detailed procedure of a hybridization method, one can refer to Nucleic Acid Hybridization Bios Scientific Publishers (1999).

The detection of the 1297T polymorphism of the GPIIIa gene using a hybridization method can be carried out by, for example, the following steps of:

(a) contacting a polynucleotide derived from a test sample with the probe according to the present invention; and (b) detecting a hybridization complex.

In step (a), mRNA prepared from the test sample or the complementary DNA (cDNA) reverse-transcribed from the mRNA, as the polynucleotide derived from the cell sample to be tested, can be contacted with the probe.

In the detection method using the probe, the probe can be labeled. An example of a label includes a label using radioactive substances, enzymes and fluorescent substances.

The detection of the hybridization product can be carried out using a well-known method such as Northern hybridization, Southern hybridization or colony hybridization.

According to the first embodiment of the method according to the present invention, the subject for which the nucleotide residue at position 1297 is identified as thymine is given the assessment that the 1297T polymorphism of the GPIIIa gene was detected, and therefore can be diagnosed or determined to be a patient with neonatal alloimmune thrombocytopenic purpura or to have the risk of developing it.

According to the second embodiment of the method according to the present invention, the subject for which the nucleotide residue at position 1297 is identified as thymine is given the assessment that the 1297T polymorphism of the GPIIIa gene is detected, and therefore can be diagnosed or determined to have a possibility of developing refractoriness to platelet transfusion therapy in platelet transfusion.

According to the detection method of the present invention, the 407S polymorphism of the GPIIIa protein in the test sample can be detected by contacting the antibody according to the present invention with the test sample and detecting the antigen-antibody reaction.

The detection of the 407S polymorphism of the GPIIIa protein using the antigen-antibody reaction can be carried out by, for example, the following steps of:

(e) contacting a protein derived from a test sample with the antibody according to the present invention; and (f) detecting an antigen-antibody complex.

A method for detecting the antigen-antibody reaction are well-known to those skilled in the art and, for example, the GPIIIa protein in a cell sample to be tested that is considered to comprise dopamine-producing neuron proliferation precursor cells, can be detected by an immunological method. For the immunological method, a previously known method such as an immunohistologic staining method, an enzyme immunoassay, a western blotting method, an agglutination method, a competition method or a sandwich method can be applied to the cell sample subjected to an appropriate treatment according to need such as separation of cells and extraction operation. The immunohistologic staining method can be carried out by, for example, a direct method using a labeled antibody or an indirect method using a labeled antibody against the antibody. For a labeling agent, a known labeling substance such as a fluorescent substance, a radioactive substance, an enzyme, a metal and a dye can be used.

According to the first embodiment of the method according to the present invention, the subject in which the antigen-antibody complex is detected is given the assessment that the 407S polymorphism of the GPIIIa protein is detected, and therefore can be diagnosed or determined to be a patient with neonatal alloimmune thrombocytopenic purpura or to have the risk of developing it.

According to the second embodiment of the method according to the present invention, the subject in which the antigen-antibody complex is detected is given the assessment that the 407S polymorphism of the GPIIIa protein is detected, and therefore can be diagnosed or determined to have a possibility of developing refractoriness to platelet transfusion therapy in platelet transfusion.

[Detection Kit]

According to the present invention, there is provided a kit for carrying out the detection method according to the present invention.

An example of a detection kit for carrying out the detection method according to the present invention includes a kit for detecting the 1297T polymorphism of the GPIIIa gene, which comprises at least the probe, the primer or the primer set according to the present invention. Further, an example of a detection kit for carrying out the detection method according to the present invention includes a kit for detecting the 407S polymorphism of the GPIIIa protein, which comprises at least the antibody according to the present invention.

The probe, primer, primer set and antibody according to the present invention may be those labeled.

The detection kit according to the present invention comprising at least the probe according to the present invention detects the 1297T polymorphism of the GPIIIa gene by the hybridization method.

The kit according to the present invention can further comprise, if desired, various reagents for carrying out the hybridization method, such as a substrate compound used for detection of the label; a hybridization buffer; an instruction; and/or an instrument.

The detection kit according to the present invention comprising at least the primer according to the present invention or the primer set according to the present invention detects the expression of the GPIIIa gene by a nucleic acid amplification method.

The kit according to the present invention can further comprise, if desired, various reagents for carrying out the nucleic acid amplification method, such as a buffer; an internal standard which indicates that PCR can proceed normally; an instruction; and/or an instrument.

The detection kit according to the present invention comprising at least the antibody according to the present invention detects the 407S polymorphism of the GPIIIa protein by detecting an antigen-antibody reaction.

The kit according to the present invention can further comprise, according to the third embodiment of the detection method, various reagents for carrying out an antigen-antibody reaction, such as a secondary antibody used for the ELISA method or the like; a coloring reagent; a buffer; an instruction; and/or an instrument.

EXAMPLES

The present invention will now be described concretely by way of Examples, but the present invention, for example, the primer sequence, probe sequence and the like, is not limited thereto.

Example 1

Relationship between Polymorphism in GPIIIa (HPA-7) Gene and Neonatal Alloimmune Thrombocytopenic Purpura With regard to the affected infant diagnosed as neonatal alloimmune thrombocytopenic purpura (NAITP), it was expected that the antibody contained in the maternal serum reacts with platelets in the affected infant. Since the affected infant was a second child, it is considered that the mother, who became sensitized to the platelet-specific antigen derived from the father during pregnancy of the first child, acquired the antibody producibility against this antigen, and platelets of the affected infant were attacked by the antibody produced during pregnancy of the second child. Since the platelet-specific antigen of the affected infant is derived from the father, it was confirmed the reactivity of the sera of the affected infant and its mother against the father's platelets by the MPHA method (Japanese Journal of Transfusion and Cell Therapy, Vol. 52. No. 6 52(6) 678-683, 2006).

First, platelets of the father were immobilized on wells of a microplate, which platelets were then subjected to reactions with sera of the affected infant and the mother, and diluents thereof. The resultants were reacted with sheep erythrocytes coated with the human IgG antibody, and the resulting images of aggregation were observed.

As a result, the serum of the mother and the serum of the affected infant, which were up to 1024-fold and 16-fold diluted, respectively, showed positive reactions against the platelets of the father.

Subsequently, the types of the platelet antigen genes were analyzed using the PCR-PHFA method (WO98/02574).

HPA-6 antibodies whereas showed a reactivity against the HPA-7b antibody. Here, since the platelets of the father reacted with the HPA-7b antibody, a certain base substitution was expected in a region corresponding to HPA-7 within the GPIIIa gene. In view of this, the exon 9 of the GPIIIa gene in the chromosomal DNA of the father was amplified using the following primers and the amplification product was purified using Wizard Plus SV Gel and PCR Clean system, followed by its ligation into the pT7Blue-T vector (manufactured by Novagen) and introduction into *E. coli* 3M109 strain (manufactured by TAKARA).

```
WHPA7-A: 5'-TCCAGAGCTGGAGTGTTAACTG  (SEQ ID NO: 9)
WHPA7-B: 5'-GTGGCAGGCACAGTGACAATC  (SEQ ID NO: 10)
```

Figure 1:
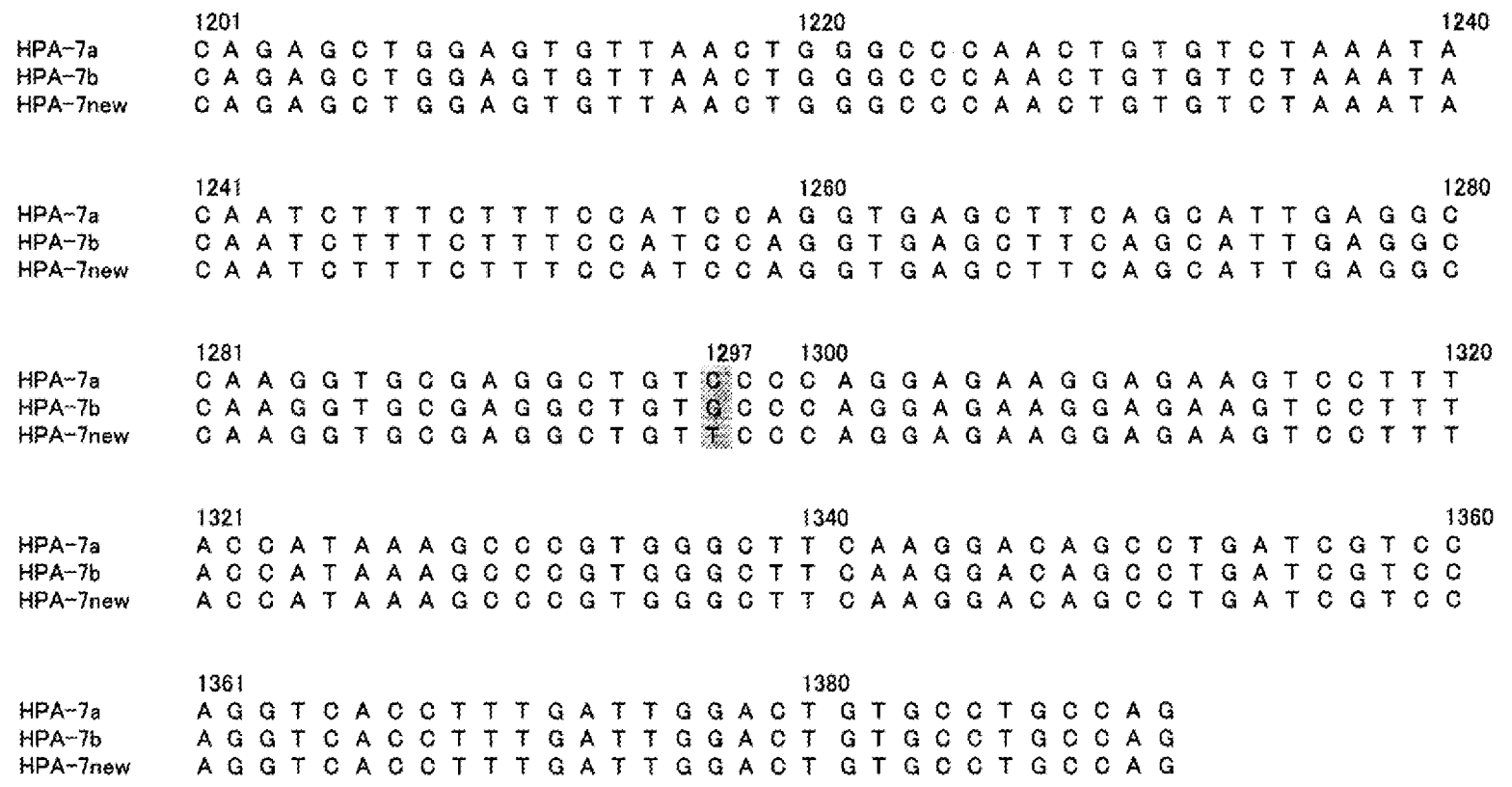

The obtained white colonies were cultured and plasmids were then purified, followed by sequencing using the M13-R18 primer (manufactured by TAKAEA) to confirm the base sequence of the cloned region. The sequencing was carried out using BigDye terminator ver.1.1 (manufactured by Applied Biosystems). The results of the sequencing were as shown in FIG. 1. HPA-7a indicates the HPA-7a gene, HPA-7b indicates the HPA-7b gene, and HPA-7new indicates a novel gene different from the HPA-7a gene and the HPA-7b gene.

TABLE 2

```
            1201                         1220                          1240
HPA-7a     C A G A G C T G G A G T G T T A A C T G  G G C C C A A C T G T G T C T A A A T A
HPA-7b     C A G A G C T G G A G T G T T A A C T G  G G C C C A A C T G T G T C T A A A T A
HPA-7new   C A G A G C T G G A G T G T T A A C T G  G G C C C A A C T G T G T C T A A A T A 1241                         1260                          1280
HPA-7a     C A A T C T T T C T T T C C A T C C A G  G T G A G C T T C A G C A T T G A G G C
HPA-7b     C A A T C T T T C T T T C C A T C C A G  G T G A G C T T C A G C A T T G A G G C
HPA-7new   C A A T C T T T C T T T C C A T C C A G  G T G A G C T T C A G C A T T G A G G C 1281                    1297 1300                          1320
HPA-7a     C A A G G T G C G A G G C T G T  C C C  A G G A G A A G G A G A A G T C C T T T
HPA-7b     C A A G G T G C G A G G C T G T  C C C  A G G A G A A G G A G A A G T C C T T T
HPA-7new   C A A G G T G C G A G G C T G T  C C C  A G G A G A A G G A G A A G T C C T T T 1321                         1340                          1360
HPA-7a     A C C A T A A A G C C C G T G G G C T T  C A A G G A C A G C C T G A T C G T C C
HPA-7b     A C C A T A A A G C C C G T G G G C T T  C A A G G A C A G C C T G A T C G T C C
HPA-7new   A C C A T A A A G C C C G T G G G C T T  C A A G G A C A G C C T G A T C G T C C 1361                         1380
HPA-7a     A G G T C A C C T T T G A T T G G A C T  G T G C C T G C C A G
HPA-7b     A G G T C A C C T T T G A T T G G A C T  G T G C C T G C C A G
HPA-7new   A G G T C A C C T T T G A T T G G A C T  G T G C C T G C C A G
```

As a result, incompatibilities were observed since, among the platelet antigens, with regard to HPA-2, the mother had (a−b+), the father had (a+b−) and the affected infant had (a+b+); and, with regard to HPA-3, the mother had (a+b−), and the father and the affected infant had (a+b+). However, with regard to the platelet antigen types of HPA-1, 4, 5 and 6, compatibilities were observed since the parents and the affected infant both had (a+b−). On the other hand, with regard to HPA-7, it was revealed that the HPA-7a gene is present whereas the HPA-7b gene is absent in all those individuals in comparison with previously reported standard DNAs for HPA-7a and HPA-7b by the PHFA method.

The platelet-specific antigen derived from the father is considered to exist in the affected infant. Thus, reactivities of the father's platelets against the known antibodies were checked, and the platelets were negative against the HPA-1 to

TABLE 3

```
           381                                        390
HPA-7a     Trp Ala Gln Leu Cys Leu Asn Thr Ile Phe
HPA-7b     Trp Ala Gln Leu Cys Leu Asn Thr Ile Phe
HPA-7new   Trp Ala Gln Leu Cys Leu Asn Thr Ile Phe 400
           Leu Ser Ile Gln Val Ser Phe Ser Ile Glu
           Leu Ser Ile Gln Val Ser Phe Ser Ile Glu
           Leu Ser Ile Gln Val Ser Phe Ser Ile Glu 407        410
           Ala Lys Val Arg Gly Cys Pro Gln Glu Lys
           Ala Lys Val Arg Gly Cys Ala Gln Glu Lys
           Ala Lys Val Arg Gly Cys Ser Gln Glu Lys
```

TABLE 3-continued

```
         411                                     420
HPA-7a   Glu Lys Ser Phe Thr Ile Lys Pro Val Gly
HPA-7b   Glu Lys Ser Phe Thr Ile Lys Pro Val Gly
HPA-7new Glu Lys Ser Phe Thr Ile Lys Pro Val Gly 430
         Phe Lys Asp Ser Leu Ile Val Gln Val Thr
         Phe Lys Asp Ser Leu Ile Val Gln Val Thr
         Phe Lys Asp Ser Leu Ile Val Gln Val Thr 440
         Phe Asp Cys Asp Cys Ala Cys Gln Ala Gln
         Phe Asp Cys Asp Cys Ala Cys Gln Ala Gln
         Phe Asp Cys Asp Cys Ala Cys Gln Ala Gln 441                             450
HPA-7a   Ala Glu Pro Asn Ser His Arg Cys Asn Asn
HPA-7b   Ala Glu Pro Asn Ser His Arg Cys Asn Asn
HPA-7new Ala Glu Pro Asn Ser His Arg Cys Asn Asn
```

As shown in FIGS. 1 and 2, it was confirmed the gene (HPA-7new) in which the base at position 1297 of the GPIIIa gene is thymine and the amino acid at position 407 of the protein produced from this gene is serine (SEQ ID NO: 7 (base sequence), SEQ ID NO: 8 (amino acid sequence)). With regard to the HPA-7 gene, as genetic polymorphisms, it has been reported so far the HPA-7a gene in which the base at position 1297 of the GPIIIa gene is cytosine and the amino acid at position 407 is proline, and the HPA-7b gene in which the base at position 1297 of the GPIIIa gene is guanine and the amino acid at position 407 is alanine, but the gene confirmed this time was confirmed to have a new sequence different from these.

Example 2

Construction of Detection System for Novel Allele of HPA-7 by PCR-PHFA Method Construction of a detection system for the novel allele of HPA-7 by the PCR-PHFA method will now be described. In the PHFA method, the product obtained by amplification of the sample using non-labeled primers (sample DNA) and the product obtained by amplification of the same region using labeled primers (standard DNA) were mixed together and heat-denatured, and it was tested whether or not the sequences of the sample DNA and the standard DNA are identical based on the extent of the chain substitution which occurs upon annealing under a temperature gradient.

(1) Preparation of Labeled Standard DNAs

Plasmids to which the HPA-7a gene, the HPA-7b gene and the novel allele (HPA-7new) confirmed in Example 1 were respectively incorporated were amplified using the following primers, to prepare PCR products of which one end was labeled with DNP (dinitrophenyl) and the other end was labeled with biotin, which products were used as standard DNAs for HPA-7a, HPA-7b and HPA-7new, respectively.

```
DNP-WHPA7-A:
5'-TCCAGAGCTGGAGTGTTAACTG    (SEQ ID NO: 11)

biotin-WHPA7-B:
5'-CTGGCAGGCACAGTCACAATC    (SEQ ID NO: 12)
```

(2) Preparation of Sample DNA

Plasmids to which HPA-7a, HPA-7b and HPA-7new were respectively incorporated were amplified by PCR using the following non-labeled primers to obtain sample DNAs. Further, chromosomal DNAs of which genotypes were known in advance were amplified with the same primers to obtain sample DNAs.

```
WHPA7-A: 5'-TCCAGAGCTGGAGTGTTAACTG    (SEQ ID NO: 9)

WHPA7-B: 5'-CTGGCAGGCACAGTCACAATC    (SEQ ID NO: 10)
```

(3) Competitive Hybridization

With 30 μl of 3×SSC (final concentration), 1 μl of a standard DNA having labels at the both ends and 20 μl of a sample DNA were mixed, and the resulting mixture was heated at 98° C. for 10 minutes, to denature the DNAs into single strands. The mixture was gradually cooled to 70° C. at a speed of 1° C./10 minutes for annealing. At this time, complementary strands having the completely matching sequence were reconstructed preferentially compared to those having a mismatch(es). That is, in cases where the sample DNA has completely the same sequence as the standard DNA, the labels at the both ends of the standard DNA are mathematically diluted, so that it is expected that the proportion of molecules having the both labels is about ½₁ of the total. In contrast, in cases where the same sequence as the standard DNA is absent in the sample DNA, the original standard DNA having the labels at the both ends was preferentially reconstructed.

(4) Detection of Reconstructed Standard DNA

Into a well of a microplate coated in advance with streptavidin, the standard DNA having the labels at the both ends was added, which DNA was retained in the well via the biotin at the terminus. By adding alkaline phosphatase labeled with an anti-DNP antibody thereto, the alkaline phosphatase is expected to be captured in the well via the standard DNA. Addition of pNPP (paranitrophenol), which is a substrate of this enzyme, thereto caused development of yellow color. This color was quantified and detected by measuring the absorbance at 405 nm. In cases where the same sequence as the standard DNA is present in a sample DNA, the absorbance is low, whereas in cases where the same sequence is absent, the absorbance is high. With regard to the Index value, the absorbance measured for each standard DNA mixed with water was defined as 100, and the proportion of the absorbance measured after mixing with each sample, heat-denaturing and the temperature gradient was shown. In cases where this value is not more than 20, the sample is judged to be positive against the standard DNA, and in cases where the value is not less than 20, the sample is judged to be negative.

For the standard DNAs prepared from the HPA-7a, HPA-7b and HPA-7new genes, the Index value exhibited by each sample DNA was measured. The results were as shown in Table 4.

|  | Standard DNA | | | | | |
|---|---|---|---|---|---|---|
|  | A405 | | | Index | | |
| Sample DNA | HPA-7a | HPA-7b | HPA-7new | HPA-7a | HPA-7b | HPA-7new |
| Positive control | 0.897 | 0.984 | 1.060 | 100 | 100 | 100 |
| HPA-7a | 0.049 | 0.529 | 0.661 | 5 | 54 | 62 |
| HPA-7b | 0.407 | 0.046 | 0.695 | 45 | 5 | 66 |
| HPA-7new | 0.577 | 0.659 | 0.050 | 64 | 67 | 5 |
| HPA-7a/b | 0.095 | 0.069 | 0.618 | 11 | 7 | 58 |
| No. 1 | 0.052 | 0.543 | 0.681 | 6 | 55 | 64 |
| No. 2 | 0.101 | 0.533 | 0.135 | 11 | 54 | 13 |
| No. 3 | 0.062 | 0.572 | 0.705 | 7 | 58 | 67 |
| No. 4 | 0.059 | 0.535 | 0.642 | 7 | 54 | 61 |
| No. 5 | 0.066 | 0.520 | 0.637 | 7 | 53 | 60 |
| No. 6 | 0.040 | 0.484 | 0.586 | 4 | 49 | 55 |
| No. 7 | 0.039 | 0.467 | 0.603 | 4 | 47 | 57 |

The sample DNAs prepared from the plasmids into which the respective genes were cloned showed low Index values against their respective standard DNAs.

Here, the Index values in the samples No. 1 and No. 3 to No. 7 were not more than 20 against HPA-7a, whereas they showed values exceeding 50 against HPA-7b and HPA-7new, so that they were assumed to have the homozygous genotype of HPA-7a. On the other hand, the sample No. 2 showed Index values of not more than 20 against the standard DNAs of HPA-7a and HPA-7new, so that it was assumed to have the heterozygous genotype of HPA-7a/new.

From the above results, it was shown that the 1297T polymorphism of the GPIIIa gene can be detected by using the PCR-PHFA method.

Example 3

Construction of Method for Detection of Novel Allele by Fluorescent Beads Method Construction of a method for detection of the novel HPA-7 allele by the fluorescent beads method will now be described. In the fluorescent beads method (Clin Chem. 43(9) p 1799-801 (1997)), 100 kinds of beads can be identified by coloring the beads with two kinds of fluorescent dyes such that 10 gradations are achieved for each dye. By immobilizing different probes on the respective beads and carrying out hybridization with sample DNAs, reactivities against the multiple DNA probes are simultaneously detected in the assay.

(1) Gene Amplification

A human chromosomal DNA was subjected to PCR amplification using the following primers according to a conventional method.

```
Biotin-P6/7FC:
5'-CCATCCAGGTGAGCTTCAGC        (SEQ ID NO: 13)

Biotin-P6/7RC-2:
5'-AGTGGTTGCAGGTATATGAGGG      (SEQ ID NO: 14)
```

(2) Preparation of Luminex Beads

As the probe sequences, oligonucleotides having the following nucleotide sequences were immobilized on Luminex beads (manufactured by Luminex) according to a conventional method.

```
Beads No. 1 (beads for detecting HPA-7a):
5'-GCTGTCCCCAGGAG-3'            (SEQ ID NO: 15)

Beads No. 2 (beads for detecting HPA-7b):
5'-GAGGCTGTGCCCAGGA-3'          (SEQ ID NO: 16)

Beads No. 3 (beads for detecting HPA-7new):
5'-GAGGCTGTTCCCAGG-3'           (SEQ ID NO: 17)

Beads No. 4 (common beads for detecting
HPA-7):
5'-TGAACCTAATAGCCATCGC-3'       (SEQ ID NO: 18)
```

(3) Hybridization and Detection

As the samples, the followings were used.

Sample No. 1: a plasmid having the HPA-7a gene

Sample No. 2: a plasmid having the HPA-7b gene

Sample No. 3: a plasmid sample having the HPA-7new gene

Sample No. 4: a chromosomal DNA No. 001

Sample No. 5: a chromosomal DNA No. 019

Sample No. 6: a chromosomal DNA No. 193

By using these as the samples, PCR amplification and hybridization with the probes were carried out, and fluorescence values of the PCR products captured by the probes bound to the beads were measured.

First, 5 µl of the PCR reaction solution was mixed with 5 µl of alkaline solution to denature the DNA into single strands. The resulting mixture was neutralized by mixing with 25 µl of a hybridization solution containing the above four kinds of beads and fluorescence-labeled streptavidin (manufactured by BD Biosciences). The resulting mixture was incubated at 55° C. for 30 minutes for hybridization of the probes with the PCR product, and fluorescence-labeling of the PCR product was carried out. Subsequently, after addition of a washing solution and mixing of the resulting mixture, the supernatant was removed by centrifugation to remove the PCR products unbound to the probes and the excess fluorescence-labeled streptavidin. The beads were suspended in the washing solution, and identification of the fluorescence-labeled PCR products hybridized with the probe on the beads and four kinds of the beads was carried out using the Luminex apparatus. The detection results were as shown in Table 5.

TABLE 5

| Sample No. | Beads No. 1 | Beads No. 2 | Beads No. 3 | Beads No. 4 |
|---|---|---|---|---|
| Sample No. 1 | 7466 | 47 | 78 | 5503 |
| Sample No. 2 | 69 | 12067 | 1649 | 5985 |
| Sample No. 3 | 128 | 594 | 12190 | 5929 |
| Sample No. 4 | 10017 | 79 | 217 | 7504 |
| Sample No. 5 | 9611 | 83 | 142 | 7836 |
| Sample No. 6 | 5355 | 174 | 9324 | 6054 |

With regard to the fluorescence values, by setting the cut-off value to 2000, the colored cells become positive. Since the sample No. 1, sample No. 2 and sample No. 3 are plasmids having the sequences of HPA-7a, HPA-7b and HPA-7new, respectively, they reacted specifically with their respective probes, to give fluorescence values higher than the cut-off value. Further, all of them reacted with the beads No. 4 having the common sequence as the probe, to give high fluorescence values. On the other hand, since the sample No. 4 and No. 5 which are chromosomal DNAs gave high fluorescence values against the beads which bind with HPA-1a and the common sequence, it can be seen that they have homozygous HPA-7a. Since the sample No. 6 gave high fluorescence values against the beads which bind with HPA-7a, HPA-7new and the common sequence, it can be seen that it has heterozygous HPA-7a and HPA-7new.

From the above results, it was shown that the 1297T polymorphism of the GPIIIa gene can be detected by using the fluorescent beads method.

The invention claimed is:

1. A complementary DNA (cDNA) comprising the nucleotide sequence of SEQ ID NO: 1, wherein a nucleotide residue at position 1297 of the nucleotide sequence of SEQ ID NO: 1 is a thymine residue.

2. The complementary DNA according to claim 1, consisting of the nucleotide sequence of SEQ ID NO: 1.

3. A primer composition comprising at least two primers having different nucleotide sequences,
   wherein at least one of the primers comprises at least 15 contiguous bases having 100% identity to SEQ ID NO: 1 including a thymine residue at a position corresponding to position 1297 of SEQ ID NO: 1, or the complementary sequence thereof, and wherein the at least one primer comprises a fluorescent label and is capable of distinguishing a mutated GPIIIa gene with a thymine residue at the position corresponding to position 1297 of SEQ ID NO: 1 from a GPIIIa gene not having a thymine residue at the position corresponding to position 1297 of SEQ ID NO: 1.

4. The primer composition according to claim 3, wherein the at least one primer comprises at least 20 contiguous bases having 100% identity to SEQ ID NO: 1 or the complementary sequence thereof.

5. A synthesized probe comprising at least 15 contiguous bases having 100% identity to SEQ ID NO: 1 including a thymine residue at a position corresponding to position 1297 of SEQ ID NO: 1, or the complementary sequence thereof,
   wherein the probe is capable of distinguishing a mutated GPIIIa gene with a thymine residue at the position corresponding to position 1297 of SEQ ID NO: 1 from a GPIIIa gene not having a thymine residue at the position corresponding to position 1297 of SEQ ID NO: 1 in a hybridization assay, and
   wherein the probe comprises a fluorescent label.

6. The synthesized probe according to claim 5, comprising 16 to 30 contiguous bases having 100% identity to SEQ ID NO: 1 or the complementary sequence thereof.

7. A kit for determining neonatal alloimmune thrombocytopenic purpura, determining a risk of developing neonatal alloimmune thrombocytopenic purpura, or determining a possibility of onset of refractoriness to platelet transfusion therapy in platelet transfusion, comprising a synthesized primer comprising at least 15 contiguous bases having 100% identity to SEQ ID NO: 1 including a thymine residue at a position corresponding to position 1297 of SEQ ID NO: 1, or the complementary sequence thereof, and a buffer suitable for a nucleic acid amplification method,
   wherein the primer comprises a fluorescent label and is capable of distinguishing a mutated GPIIIa gene with a thymine residue at the position corresponding to position 1297 of SEQ ID NO: 1 from a GPIIIa gene not having a thymine residue at the position corresponding to position 1297 of SEQ ID NO:1.

8. A kit for determining neonatal alloimmune thrombocytopenic purpura, determining a risk of developing neonatal alloimmune thrombocytopenic purpura, or determining a possibility of onset of refractoriness to platelet transfusion therapy in platelet transfusion, comprising a synthesized probe comprising at least 15 contiguous bases having 100% identity to SEQ ID NO: 1 including a thymine residue at a position corresponding to position 1297 of SEQ ID NO:1 or the complementary sequence thereof and a hybridization buffer,
   wherein the probe is capable of distinguishing a mutated GPIIIa gene with a thymine residue at the position corresponding to position 1297 of SEQ ID NO: 1 from a GPIIIa gene not having a thymine residue at the position corresponding to position 1297 of SEQ ID NO: 1 in a hybridization assay and wherein the probe comprises a fluorescent label.

9. A method for detecting a mutation in a GPIIIa gene, comprising isolating a sample and detecting the mutation in the GPIIIa gene,
   wherein the detection is via a hybridization method with a synthesized probe comprising at least 15 contiguous bases having 100% identity to SEQ ID NO:1 including a thymine residue at a position corresponding to position 1297 of SEQ ID NO:1 or the complementary sequence thereof, and wherein the probe is capable of distinguishing a mutated GPIIIa gene with a thymine residue at the position corresponding to position 1297 of SEQ ID NO: 1 from a GPIIIa gene not having a thymine residue at the position corresponding to position 1297 of SEQ ID NO: 1.

10. The method of claim 9, wherein the sample is obtained from a newborn or a blood relative of the newborn.

11. The method of claim 9, wherein the sample is obtained from a patient to receive a platelet transfusion.

12. A synthesized probe comprising at least 15 contiguous bases having 100% identity to SEQ ID NO: 1 and comprising the thymine residue at a position corresponding to position 1297 of SEQ ID NO: 1 or the complementary sequence thereof,
   wherein the probe is capable of distinguishing a mutated GPIIIa gene with a thymine residue at the position corresponding to position 1297 of SEQ ID NO: 1 from a GPIIIa gene not having a thymine residue at the position corresponding to position 1297 of SEQ ID NO: 1 in a hybridization assay, and
   wherein the probe is immobilized on a bead.

13. The synthesized probe according to claim 12, comprising 16 to 30 contiguous bases having 100% identity to SEQ ID NO: 1 or the complementary sequence thereof.

* * * * *

SEQUENCE LISTING

<160> NUMBER OF SEQ ID NOS: 24

<210> SEQ ID NO 1
<211> LENGTH: 4469
<212> TYPE: DNA
<213> ORGANISM: Homo sapiens
<220> FEATURE:
<221> NAME/KEY: CDS
<222> LOCATION: (79)..(2364)

<400> SEQUENCE: 1

```
atgcgagcgc ggccgcggcc ccggccgctc tgggtgactg tgctggcgct gggggcgctg      60
gcgggcgttg gcgtagga ggg ccc aac atc tgt acc acg cga ggt gtg agc      111
                    Gly Pro Asn Ile Cys Thr Thr Arg Gly Val Ser
                     1               5                      10 tcc tgc cag cag tgc ctg gct gtg agc ccc atg tgt gcc tgg tgc tct      159
Ser Cys Gln Gln Cys Leu Ala Val Ser Pro Met Cys Ala Trp Cys Ser
            15                  20                  25 gat gag gcc ctg cct ctg ggc tca cct cgc tgt gac ctg aag gag aat      207
Asp Glu Ala Leu Pro Leu Gly Ser Pro Arg Cys Asp Leu Lys Glu Asn
        30                  35                  40 ctg ctg aag gat aac tgt gcc cca gaa tcc atc gag ttc cca gtg agt      255
Leu Leu Lys Asp Asn Cys Ala Pro Glu Ser Ile Glu Phe Pro Val Ser
    45                  50                  55 gag gcc cga gta cta gag gac agg ccc ctc agc gac aag ggc tct gga      303
Glu Ala Arg Val Leu Glu Asp Arg Pro Leu Ser Asp Lys Gly Ser Gly
60                  65                  70                  75 gac agc tcc cag gtc act caa gtc agt ccc cag agg att gca ctc cgg      351
Asp Ser Ser Gln Val Thr Gln Val Ser Pro Gln Arg Ile Ala Leu Arg
                80                  85                  90 ctc cgg cca gat gat tcg aag aat ttc tcc atc caa gtg cgg cag gtg      399
Leu Arg Pro Asp Asp Ser Lys Asn Phe Ser Ile Gln Val Arg Gln Val
            95                  100                 105 gag gat tac cct gtg gac atc tac tac ttg atg gac ctg tct tac tcc      447
Glu Asp Tyr Pro Val Asp Ile Tyr Tyr Leu Met Asp Leu Ser Tyr Ser
        110                 115                 120 atg aag gat gat ctg tgg agc atc cag aac ctg ggt acc aag ctg gcc      495
Met Lys Asp Asp Leu Trp Ser Ile Gln Asn Leu Gly Thr Lys Leu Ala
    125                 130                 135 acc cag atg cga aag ctc acc agt aac ctg cgg att ggc ttc ggg gca      543
Thr Gln Met Arg Lys Leu Thr Ser Asn Leu Arg Ile Gly Phe Gly Ala
140                 145                 150                 155 ttt gtg gac aag cct gtg tca cca tac atg tat atc tcc cca cca gag      591
Phe Val Asp Lys Pro Val Ser Pro Tyr Met Tyr Ile Ser Pro Pro Glu
                160                 165                 170
```

-continued

| | | |
|---|---|---|
| gcc ctc gaa aac ccc tgc tat gat atg aag acc acc tgc ttg ccc atg<br>Ala Leu Glu Asn Pro Cys Tyr Asp Met Lys Thr Thr Cys Leu Pro Met<br>    175                 180                 185 | 639 |
| ttt ggc tac aaa cac gtg ctg acg cta act gac cag gtg acc cgc ttc<br>Phe Gly Tyr Lys His Val Leu Thr Leu Thr Asp Gln Val Thr Arg Phe<br>    190                 195                 200 | 687 |
| aat gag gaa gtg aag aag cag agt gtg tca cgg aac cga gat gcc cca<br>Asn Glu Glu Val Lys Lys Gln Ser Val Ser Arg Asn Arg Asp Ala Pro<br>205                 210                 215 | 735 |
| gag ggt ggc ttt gat gcc atc atg cag gct aca gtc tgt gat gaa aag<br>Glu Gly Gly Phe Asp Ala Ile Met Gln Ala Thr Val Cys Asp Glu Lys<br>220                 225                 230                 235 | 783 |
| att ggc tgg agg aat gat gca tcc cac ttg ctg gtg ttt acc act gat<br>Ile Gly Trp Arg Asn Asp Ala Ser His Leu Leu Val Phe Thr Thr Asp<br>            240                 245                 250 | 831 |
| gcc aag act cat ata gca ttg gac gga agg ctg gca ggc att gtc cag<br>Ala Lys Thr His Ile Ala Leu Asp Gly Arg Leu Ala Gly Ile Val Gln<br>                255                 260                 265 | 879 |
| cct aat gac ggg cag tgt cat gtt ggt agt gac aat cat tac tct gcc<br>Pro Asn Asp Gly Gln Cys His Val Gly Ser Asp Asn His Tyr Ser Ala<br>    270                 275                 280 | 927 |
| tcc act acc atg gat tat ccc tct ttg ggg ctg atg act gag aag cta<br>Ser Thr Thr Met Asp Tyr Pro Ser Leu Gly Leu Met Thr Glu Lys Leu<br>285                 290                 295 | 975 |
| tcc cag aaa aac atc aat ttg atc ttt gca gtg act gaa aat gta gtc<br>Ser Gln Lys Asn Ile Asn Leu Ile Phe Ala Val Thr Glu Asn Val Val<br>300                 305                 310                 315 | 1023 |
| aat ctc tat cag aac tat agt gag ctc atc cca ggg acc aca gtt ggg<br>Asn Leu Tyr Gln Asn Tyr Ser Glu Leu Ile Pro Gly Thr Thr Val Gly<br>            320                 325                 330 | 1071 |
| gtt ctg tcc atg gat tcc agc aat gtc ctc cag ctc att gtt gat gct<br>Val Leu Ser Met Asp Ser Ser Asn Val Leu Gln Leu Ile Val Asp Ala<br>                335                 340                 345 | 1119 |
| tat ggg aaa atc cgt tct aaa gtc gag ctg gaa gtg cgt gac ctc cct<br>Tyr Gly Lys Ile Arg Ser Lys Val Glu Leu Glu Val Arg Asp Leu Pro<br>    350                 355                 360 | 1167 |
| gaa gag ttg tct cta tcc ttc aat gcc acc tgc ctc aac aat gag gtc<br>Glu Glu Leu Ser Leu Ser Phe Asn Ala Thr Cys Leu Asn Asn Glu Val<br>365                 370                 375 | 1215 |
| atc cct ggc ctc aag tct tgt atg gga ctc aag att gga gac acg gtg<br>Ile Pro Gly Leu Lys Ser Cys Met Gly Leu Lys Ile Gly Asp Thr Val<br>380                 385                 390                 395 | 1263 |
| agc ttc agc att gag gcc aag gtg cga ggc tgt tcc cag gag aag gag<br>Ser Phe Ser Ile Glu Ala Lys Val Arg Gly Cys Ser Gln Glu Lys Glu<br>            400                 405                 410 | 1311 |
| aag tcc ttt acc ata aag ccc gtg ggc ttc aag gac agc ctg atc gtc<br>Lys Ser Phe Thr Ile Lys Pro Val Gly Phe Lys Asp Ser Leu Ile Val<br>                415                 420                 425 | 1359 |
| cag gtc acc ttt gat tgt gac tgt gcc tgc cag gcc caa gct gaa cct<br>Gln Val Thr Phe Asp Cys Asp Cys Ala Cys Gln Ala Gln Ala Glu Pro<br>    430                 435                 440 | 1407 |
| aat agc cat cgc tgc aac aat ggc aat ggg acc ttt gag tgt ggg gta<br>Asn Ser His Arg Cys Asn Asn Gly Asn Gly Thr Phe Glu Cys Gly Val<br>445                 450                 455 | 1455 |
| tgc cgt tgt ggg cct ggc tgg ctg gga tcc cag tgt gag tgc tca gag<br>Cys Arg Cys Gly Pro Gly Trp Leu Gly Ser Gln Cys Glu Cys Ser Glu<br>460                 465                 470                 475 | 1503 |
| gag gac tat cgc cct tcc cag cag gac gag tgc agc ccc cgg gag ggt<br>Glu Asp Tyr Arg Pro Ser Gln Gln Asp Glu Cys Ser Pro Arg Glu Gly | 1551 |

-continued

|     |     |     | 480 |     |     |     | 485 |     |     |     | 490 |     |     |     |      |
|-----|-----|-----|-----|-----|-----|-----|-----|-----|-----|-----|-----|-----|-----|-----|------|

```
cag ccc gtc tgc agc cag cgg ggc gag tgc ctc tgt ggt caa tgt gtc      1599
Gln Pro Val Cys Ser Gln Arg Gly Glu Cys Leu Cys Gly Gln Cys Val
            495                 500                 505 tgc cac agc agt gac ttt ggc aag atc acg ggc aag tac tgc gag tgt      1647
Cys His Ser Ser Asp Phe Gly Lys Ile Thr Gly Lys Tyr Cys Glu Cys
        510                 515                 520 gac gac ttc tcc tgt gtc cgc tac aag ggg gag atg tgc tca ggc cat      1695
Asp Asp Phe Ser Cys Val Arg Tyr Lys Gly Glu Met Cys Ser Gly His
525                 530                 535 ggc cag tgc agc tgt ggg gac tgc ctg tgt gac tcc gac tgg acc ggc      1743
Gly Gln Cys Ser Cys Gly Asp Cys Leu Cys Asp Ser Asp Trp Thr Gly
540                 545                 550                 555 tac tac tgc aac tgt acc acg cgt act gac acc tgc atg tcc agc aat      1791
Tyr Tyr Cys Asn Cys Thr Thr Arg Thr Asp Thr Cys Met Ser Ser Asn
                560                 565                 570 ggg ctg ctg tgc agc ggc cgc ggc aag tgt gaa tgt ggc agc tgt gtc      1839
Gly Leu Leu Cys Ser Gly Arg Gly Lys Cys Glu Cys Gly Ser Cys Val
            575                 580                 585 tgt atc cag ccg ggc tcc tat ggg gac acc tgt gag aag tgc ccc acc      1887
Cys Ile Gln Pro Gly Ser Tyr Gly Asp Thr Cys Glu Lys Cys Pro Thr
        590                 595                 600 tgc cca gat gcc tgc acc ttt aag aaa gaa tgt gtg gag tgt aag aag      1935
Cys Pro Asp Ala Cys Thr Phe Lys Lys Glu Cys Val Glu Cys Lys Lys
605                 610                 615 ttt gac cgg gga gcc cta cat gac gaa aat acc tgc aac cgt tac tgc      1983
Phe Asp Arg Gly Ala Leu His Asp Glu Asn Thr Cys Asn Arg Tyr Cys
620                 625                 630                 635 cgt gac gag att gag tca gtg aaa gag ctt aag gac act ggc aag gat      2031
Arg Asp Glu Ile Glu Ser Val Lys Glu Leu Lys Asp Thr Gly Lys Asp
                640                 645                 650 gca gtg aat tgt acc tat aag aat gag gat gac tgt gtc gtc aga ttc      2079
Ala Val Asn Cys Thr Tyr Lys Asn Glu Asp Asp Cys Val Val Arg Phe
            655                 660                 665 cag tac tat gaa gat tct agt gga aag tcc atc ctg tat gtg gta gaa      2127
Gln Tyr Tyr Glu Asp Ser Ser Gly Lys Ser Ile Leu Tyr Val Val Glu
        670                 675                 680 gag cca gag tgt ccc aag ggc cct gac atc ctg gtg gtc ctg ctc tca      2175
Glu Pro Glu Cys Pro Lys Gly Pro Asp Ile Leu Val Val Leu Leu Ser
685                 690                 695 gtg atg ggg gcc att ctg ctc att ggc ctt gcc gcc ctg ctc atc tgg      2223
Val Met Gly Ala Ile Leu Leu Ile Gly Leu Ala Ala Leu Leu Ile Trp
700                 705                 710                 715 aaa ctc ctc atc acc atc cac gac cga aaa gaa ttc gct aaa ttt gag      2271
Lys Leu Leu Ile Thr Ile His Asp Arg Lys Glu Phe Ala Lys Phe Glu
                720                 725                 730 gaa gaa cgc gcc aga gca aaa tgg gac aca gcc aac aac cca ctg tat      2319
Glu Glu Arg Ala Arg Ala Lys Trp Asp Thr Ala Asn Asn Pro Leu Tyr
            735                 740                 745 aaa gag gcc acg tct acc ttc acc aat atc acg tac cgg ggc act          2364
Lys Glu Ala Thr Ser Thr Phe Thr Asn Ile Thr Tyr Arg Gly Thr
        750                 755                 760 taatgataag cagtcatcct cagatcatta tcagcctgtg ccaggattgc aggagtccct    2424
gccatcatgt ttacagagga cagtatttgt ggggagggat tcggggctc agagtggggt     2484 aggttgggag aatgtcagta tgtggaagtg tgggtctgtg tgtgtgtatg tgggggtctg    2544
tgtgtttatg tgtgtgtgtt gtgtgtggga gtgtgtaatt taaaattgtg atgtgtcctg    2604
ataagctgag ctccttagcc tttgtcccag aatgcctcct gcagggattc ttcctgctta    2664
```

-continued

```
gcttgagggt gactatggag ctgagcaggt gttcttcatt acctcagtga gaagccagct    2724
ttcctcatca ggccattgtc cctgaagaga agggcagggc tgaggcctct cattccagag    2784
gaagggacac caagccttgg ctctaccctg agttcataaa tttatggttc tcaggcctga    2844
ctctcagcag ctatggtagg aactgctggc ttggcagccc gggtcatctg tacctctgcc    2904
tcctttcccc tccctcaggc cgaaggagga gtcagggaga gctgaactat tagagctgcc    2964
tgtgcctttt gccatcccct caacccagct atggttctct cgcaagggaa gtccttgcaa    3024
gctaattctt tgacctgttg ggagtgagga tgtctgggcc actcaggggt cattcatggc    3084
ctgggggatg taccagcatc tcccagttca taatcacaac ccttcaaaga tttgccttat    3144
tggcagctct actctggagg tttgtttaga agaagtgtgt cacccttagg ccagcaccat    3204
ctctttacct cctaattcca caccctcact gctgtagaca tttgctatga cctggggatg    3264
tctctcatga ccaaatgctt ttcctcaaag ggagagagtg ctattgtaga gccagaggtc    3324 tggcccctatg cttccggcct cctgtccctc atccatagca cctccacata cctggccctg    3384
agccttggtg tgctgtatcc atccatgggg ctgattgtat ttaccttcta cctcttggct    3444
gccttgtgaa ggaattattc ccatgagttg gctgggaata agtgccagga tggaatgatg    3504
ggtcagttgt atcagcacgt gtggcctgtt cttctatggg ttacaacctc atttaactca    3564
gtctttaatc tgagaggcca cagtgcaatt ttattttatt tttctcatga tgaggttttc    3624
ttaacttaaa agaacatgta tataaacatg cttgcattat atttgtaaat ttatgtgtat    3684
ggcaaagaag gagagcatag gaaaccacac agacttgggc agggtacaga cactcccact    3744
tggcatcatt cacagcaagt cactggccag tggctggatc tgtgaggggc tctctcatga    3804
tagaaggcta tggggataga tgtgtggaca cattggacct ttcctgagga agagggactg    3864
ttcttttgtc ccagaaaagc agtggctcca ttggtgttga catacatcca acattaaaag    3924 ccaccccccaa atgcccaaga aaaaagaaa gacttatcaa catttgttcc atgagcagaa    3984
aactggagct ctggcctcag tgttacagct aaataatctt taattaaggc aagtcacttt    4044
cttcttctta aagctgtttc tagtttgaga atgatggga ttttagcagc cagtcttgaa    4104
ggtctctttc agtatcaaca ttctaagatg ctgggactta ctgtgtcatc aaatgtgcgg    4164
ttaagattct ctgggatatt gatactgttt gtgtttttag ttgggagatc tgagagacct    4224
ggctttggca agagcagatg tcattccata tcacctttct caatgaaagt ctcattctat    4284
cctctctcca aacccgtttt ccaacatttg ttaatagtta cgtctctcct gatgtagcac    4344
ttaagcttca tttagttatt atttctttct tcactttgca cacatttgca tccacatatt    4404
agggaaggaa taagtagctg caaactatct attcctgtat tattgtgtta acattgagat    4464
aaacc                                                                4469
```

<210> SEQ ID NO 2
<211> LENGTH: 762
<212> TYPE: PRT
<213> ORGANISM: Homo sapiens

<400> SEQUENCE: 2

```
Gly Pro Asn Ile Cys Thr Thr Arg Gly Val Ser Ser Cys Gln Gln Cys
 1               5                  10                  15

Leu Ala Val Ser Pro Met Cys Ala Trp Cys Ser Asp Glu Ala Leu Pro
            20                  25                  30

Leu Gly Ser Pro Arg Cys Asp Leu Lys Glu Asn Leu Leu Lys Asp Asn
        35                  40                  45
```

-continued

```
Cys Ala Pro Glu Ser Ile Glu Phe Pro Val Ser Glu Ala Arg Val Leu
    50              55                  60
Glu Asp Arg Pro Leu Ser Asp Lys Gly Ser Gly Asp Ser Ser Gln Val
65                  70                  75                  80
Thr Gln Val Ser Pro Gln Arg Ile Ala Leu Arg Leu Arg Pro Asp Asp
                85                  90                  95
Ser Lys Asn Phe Ser Ile Gln Val Arg Gln Val Glu Asp Tyr Pro Val
               100                 105                 110
Asp Ile Tyr Tyr Leu Met Asp Leu Ser Tyr Ser Met Lys Asp Asp Leu
           115                 120                 125
Trp Ser Ile Gln Asn Leu Gly Thr Lys Leu Ala Thr Gln Met Arg Lys
   130                 135                 140
Leu Thr Ser Asn Leu Arg Ile Gly Phe Gly Ala Phe Val Asp Lys Pro
145                 150                 155                 160
Val Ser Pro Tyr Met Tyr Ile Ser Pro Pro Glu Ala Leu Glu Asn Pro
               165                 170                 175
Cys Tyr Asp Met Lys Thr Thr Cys Leu Pro Met Phe Gly Tyr Lys His
           180                 185                 190
Val Leu Thr Leu Thr Asp Gln Val Thr Arg Phe Asn Glu Glu Val Lys
   195                 200                 205
Lys Gln Ser Val Ser Arg Asn Arg Asp Ala Pro Glu Gly Gly Phe Asp
210                 215                 220
Ala Ile Met Gln Ala Thr Val Cys Asp Glu Lys Ile Gly Trp Arg Asn
225                 230                 235                 240
Asp Ala Ser His Leu Leu Val Phe Thr Thr Asp Ala Lys Thr His Ile
               245                 250                 255
Ala Leu Asp Gly Arg Leu Ala Gly Ile Val Gln Pro Asn Asp Gly Gln
           260                 265                 270
Cys His Val Gly Ser Asp Asn His Tyr Ser Ala Ser Thr Thr Met Asp
   275                 280                 285
Tyr Pro Ser Leu Gly Leu Met Thr Glu Lys Leu Ser Gln Lys Asn Ile
290                 295                 300
Asn Leu Ile Phe Ala Val Thr Glu Asn Val Val Asn Leu Tyr Gln Asn
305                 310                 315                 320
Tyr Ser Glu Leu Ile Pro Gly Thr Thr Val Gly Val Leu Ser Met Asp
               325                 330                 335
Ser Ser Asn Val Leu Gln Leu Ile Val Asp Ala Tyr Gly Lys Ile Arg
           340                 345                 350
Ser Lys Val Glu Leu Glu Val Arg Asp Leu Pro Glu Glu Leu Ser Leu
   355                 360                 365
Ser Phe Asn Ala Thr Cys Leu Asn Asn Glu Val Ile Pro Gly Leu Lys
370                 375                 380
Ser Cys Met Gly Leu Lys Ile Gly Asp Thr Val Ser Phe Ser Ile Glu
385                 390                 395                 400
Ala Lys Val Arg Gly Cys Ser Gln Glu Lys Glu Lys Ser Phe Thr Ile
               405                 410                 415
Lys Pro Val Gly Phe Lys Asp Ser Leu Ile Val Gln Val Thr Phe Asp
           420                 425                 430
Cys Asp Cys Ala Cys Gln Ala Gln Ala Glu Pro Asn Ser His Arg Cys
   435                 440                 445
Asn Asn Gly Asn Gly Thr Phe Glu Cys Gly Val Cys Arg Cys Gly Pro
450                 455                 460
```

```
Gly Trp Leu Gly Ser Gln Cys Glu Cys Ser Glu Asp Tyr Arg Pro
465                 470                 475                 480

Ser Gln Gln Asp Glu Cys Ser Pro Arg Glu Gly Gln Pro Val Cys Ser
            485                 490                 495

Gln Arg Gly Glu Cys Leu Cys Gly Gln Cys Val Cys His Ser Ser Asp
            500                 505                 510

Phe Gly Lys Ile Thr Gly Lys Tyr Cys Glu Cys Asp Asp Phe Ser Cys
            515                 520                 525

Val Arg Tyr Lys Gly Glu Met Cys Ser Gly His Gly Gln Cys Ser Cys
            530                 535                 540

Gly Asp Cys Leu Cys Asp Ser Asp Trp Thr Gly Tyr Tyr Cys Asn Cys
545                 550                 555                 560

Thr Thr Arg Thr Asp Thr Cys Met Ser Ser Asn Gly Leu Leu Cys Ser
                565                 570                 575

Gly Arg Gly Lys Cys Glu Cys Gly Ser Cys Val Cys Ile Gln Pro Gly
            580                 585                 590

Ser Tyr Gly Asp Thr Cys Glu Lys Cys Pro Thr Cys Pro Asp Ala Cys
            595                 600                 605

Thr Phe Lys Lys Glu Cys Val Glu Cys Lys Lys Phe Asp Arg Gly Ala
610                 615                 620

Leu His Asp Glu Asn Thr Cys Asn Arg Tyr Cys Arg Asp Glu Ile Glu
625                 630                 635                 640

Ser Val Lys Glu Leu Lys Asp Thr Gly Lys Asp Ala Val Asn Cys Thr
                645                 650                 655

Tyr Lys Asn Glu Asp Asp Cys Val Val Arg Phe Gln Tyr Tyr Glu Asp
            660                 665                 670

Ser Ser Gly Lys Ser Ile Leu Tyr Val Val Glu Glu Pro Glu Cys Pro
            675                 680                 685

Lys Gly Pro Asp Ile Leu Val Val Leu Leu Ser Val Met Gly Ala Ile
            690                 695                 700

Leu Leu Ile Gly Leu Ala Ala Leu Leu Ile Trp Lys Leu Leu Ile Thr
705                 710                 715                 720

Ile His Asp Arg Lys Glu Phe Ala Lys Phe Glu Glu Glu Arg Ala Arg
                725                 730                 735

Ala Lys Trp Asp Thr Ala Asn Asn Pro Leu Tyr Lys Glu Ala Thr Ser
            740                 745                 750

Thr Phe Thr Asn Ile Thr Tyr Arg Gly Thr
                755                 760

<210> SEQ ID NO 3
<211> LENGTH: 40
<212> TYPE: DNA
<213> ORGANISM: Homo sapiens

<400> SEQUENCE: 3
caaggtgcga ggctgttccc aggagaagga gaagtccttt                            40

<210> SEQ ID NO 4
<211> LENGTH: 26
<212> TYPE: PRT
<213> ORGANISM: Homo sapiens

<400> SEQUENCE: 4

Val Ser Phe Ser Ile Glu Ala Lys Val Arg Gly Cys Ser Gln Glu Lys
1               5                   10                  15

Glu Lys Ser Phe Thr Ile Lys Pro Val Gly
```

```
                    20                  25

<210> SEQ ID NO 5
<211> LENGTH: 4469
<212> TYPE: DNA
<213> ORGANISM: Homo sapiens
<220> FEATURE:
<221> NAME/KEY: CDS
<222> LOCATION: (79)..(2364)

<400> SEQUENCE: 5
atgcgagcgc ggccgcggcc ccggccgctc tgggtgactg tgctggcgct gggggcgctg      60
gcgggcgttg cgtagga ggg ccc aac atc tgt acc acg cga ggt gtg agc        111
                   Gly Pro Asn Ile Cys Thr Thr Arg Gly Val Ser
                    1               5                  10 tcc tgc cag cag tgc ctg gct gtg agc ccc atg tgt gcc tgg tgc tct      159
Ser Cys Gln Gln Cys Leu Ala Val Ser Pro Met Cys Ala Trp Cys Ser
         15                  20                  25 gat gag gcc ctg cct ctg ggc tca cct cgc tgt gac ctg aag gag aat      207
Asp Glu Ala Leu Pro Leu Gly Ser Pro Arg Cys Asp Leu Lys Glu Asn
     30                  35                  40 ctg ctg aag gat aac tgt gcc cca gaa tcc atc gag ttc cca gtg agt      255
Leu Leu Lys Asp Asn Cys Ala Pro Glu Ser Ile Glu Phe Pro Val Ser
 45                  50                  55 gag gcc cga gta cta gag gac agg ccc ctc agc gac aag ggc tct gga      303
Glu Ala Arg Val Leu Glu Asp Arg Pro Leu Ser Asp Lys Gly Ser Gly
 60                  65                  70                  75 gac agc tcc cag gtc act caa gtc agt ccc cag agg att gca ctc cgg      351
Asp Ser Ser Gln Val Thr Gln Val Ser Pro Gln Arg Ile Ala Leu Arg
                 80                  85                  90 ctc cgg cca gat gat tcg aag aat ttc tcc atc caa gtg cgg cag gtg      399
Leu Arg Pro Asp Asp Ser Lys Asn Phe Ser Ile Gln Val Arg Gln Val
             95                 100                 105 gag gat tac cct gtg gac atc tac tac ttg atg gac ctg tct tac tcc      447
Glu Asp Tyr Pro Val Asp Ile Tyr Tyr Leu Met Asp Leu Ser Tyr Ser
        110                 115                 120 atg aag gat gat ctg tgg agc atc cag aac ctg ggt acc aag ctg gcc      495
Met Lys Asp Asp Leu Trp Ser Ile Gln Asn Leu Gly Thr Lys Leu Ala
    125                 130                 135 acc cag atg cga aag ctc acc agt aac ctg cgg att ggc ttc ggg gca      543
Thr Gln Met Arg Lys Leu Thr Ser Asn Leu Arg Ile Gly Phe Gly Ala
140                 145                 150                 155 ttt gtg gac aag cct gtg tca cca tac atg tat atc tcc cca cca gag      591
Phe Val Asp Lys Pro Val Ser Pro Tyr Met Tyr Ile Ser Pro Pro Glu
                160                 165                 170 gcc ctc gaa aac ccc tgc tat gat atg aag acc acc tgc ttg ccc atg      639
Ala Leu Glu Asn Pro Cys Tyr Asp Met Lys Thr Thr Cys Leu Pro Met
            175                 180                 185 ttt ggc tac aaa cac gtg ctg acg cta act gac cag gtg acc cgc ttc      687
Phe Gly Tyr Lys His Val Leu Thr Leu Thr Asp Gln Val Thr Arg Phe
        190                 195                 200 aat gag gaa gtg aag aag cag agt gtg tca cgg aac cga gat gcc cca      735
Asn Glu Glu Val Lys Lys Gln Ser Val Ser Arg Asn Arg Asp Ala Pro
    205                 210                 215 gag ggt ggc ttt gat gcc atc atg cag gct aca gtc tgt gat gaa aag      783
Glu Gly Gly Phe Asp Ala Ile Met Gln Ala Thr Val Cys Asp Glu Lys
220                 225                 230                 235 att ggc tgg agg aat gat gca tcc cac ttg ctg gtg ttt acc act gat      831
Ile Gly Trp Arg Asn Asp Ala Ser His Leu Leu Val Phe Thr Thr Asp
                240                 245                 250
```

```
                                                            -continued gcc aag act cat ata gca ttg gac gga agg ctg gca ggc att gtc cag      879
Ala Lys Thr His Ile Ala Leu Asp Gly Arg Leu Ala Gly Ile Val Gln
            255                 260                 265 cct aat gac ggg cag tgt cat gtt ggt agt gac aat cat tac tct gcc      927
Pro Asn Asp Gly Gln Cys His Val Gly Ser Asp Asn His Tyr Ser Ala
            270                 275                 280 tcc act acc atg gat tat ccc tct ttg ggg ctg atg act gag aag cta      975
Ser Thr Thr Met Asp Tyr Pro Ser Leu Gly Leu Met Thr Glu Lys Leu
        285                 290                 295 tcc cag aaa aac atc aat ttg atc ttt gca gtg act gaa aat gta gtc     1023
Ser Gln Lys Asn Ile Asn Leu Ile Phe Ala Val Thr Glu Asn Val Val
300                 305                 310                 315 aat ctc tat cag aac tat agt gag ctc atc cca ggg acc aca gtt ggg     1071
Asn Leu Tyr Gln Asn Tyr Ser Glu Leu Ile Pro Gly Thr Thr Val Gly
                320                 325                 330 gtt ctg tcc atg gat tcc agc aat gtc ctc cag ctc att gtt gat gct     1119
Val Leu Ser Met Asp Ser Ser Asn Val Leu Gln Leu Ile Val Asp Ala
            335                 340                 345 tat ggg aaa atc cgt tct aaa gtc gag ctg gaa gtg cgt gac ctc cct     1167
Tyr Gly Lys Ile Arg Ser Lys Val Glu Leu Glu Val Arg Asp Leu Pro
        350                 355                 360 gaa gag ttg tct cta tcc ttc aat gcc acc tgc ctc aac aat gag gtc     1215
Glu Glu Leu Ser Leu Ser Phe Asn Ala Thr Cys Leu Asn Asn Glu Val
365                 370                 375 atc cct ggc ctc aag tct tgt atg gga ctc aag att gga gac acg gtg     1263
Ile Pro Gly Leu Lys Ser Cys Met Gly Leu Lys Ile Gly Asp Thr Val
                380                 385                 390                 395 agc ttc agc att gag gcc aag gtg cga ggc tgt ccc cag gag aag gag     1311
Ser Phe Ser Ile Glu Ala Lys Val Arg Gly Cys Pro Gln Glu Lys Glu
            400                 405                 410 aag tcc ttt acc ata aag ccc gtg ggc ttc aag gac agc ctg atc gtc     1359
Lys Ser Phe Thr Ile Lys Pro Val Gly Phe Lys Asp Ser Leu Ile Val
        415                 420                 425 cag gtc acc ttt gat tgt gac tgt gcc tgc cag gcc caa gct gaa cct     1407
Gln Val Thr Phe Asp Cys Asp Cys Ala Cys Gln Ala Gln Ala Glu Pro
                430                 435                 440 aat agc cat cgc tgc aac aat ggc aat ggg acc ttt gag tgt ggg gta     1455
Asn Ser His Arg Cys Asn Asn Gly Asn Gly Thr Phe Glu Cys Gly Val
445                 450                 455 tgc cgt tgt ggg cct ggc tgg ctg gga tcc cag tgt gag tgc tca gag     1503
Cys Arg Cys Gly Pro Gly Trp Leu Gly Ser Gln Cys Glu Cys Ser Glu
460                 465                 470                 475 gag gac tat cgc cct tcc cag cag gac gag tgc agc ccc cgg gag ggt     1551
Glu Asp Tyr Arg Pro Ser Gln Gln Asp Glu Cys Ser Pro Arg Glu Gly
                480                 485                 490 cag ccc gtc tgc agc cag cgg ggc gag tgc ctc tgt ggt caa tgt gtc     1599
Gln Pro Val Cys Ser Gln Arg Gly Glu Cys Leu Cys Gly Gln Cys Val
            495                 500                 505 tgc cac agc agt gac ttt ggc aag atc acg ggc aag tac tgc gag tgt     1647
Cys His Ser Ser Asp Phe Gly Lys Ile Thr Gly Lys Tyr Cys Glu Cys
        510                 515                 520 gac gac ttc tcc tgt gtc cgc tac aag ggg gag atg tgc tca ggc cat     1695
Asp Asp Phe Ser Cys Val Arg Tyr Lys Gly Glu Met Cys Ser Gly His
525                 530                 535 ggc cag tgc agc tgt ggg gac tgc ctg tgt gac tcc gac tgg acc ggc     1743
Gly Gln Cys Ser Cys Gly Asp Cys Leu Cys Asp Ser Asp Trp Thr Gly
540                 545                 550                 555 tac tac tgc aac tgt acc acg cgt act gac acc tgc atg tcc agc aat     1791
Tyr Tyr Cys Asn Cys Thr Thr Arg Thr Asp Thr Cys Met Ser Ser Asn
            560                 565                 570
```

| | |
|---|---|
| ggg ctg ctg tgc agc ggc cgc ggc aag tgt gaa tgt ggc agc tgt gtc<br>Gly Leu Leu Cys Ser Gly Arg Gly Lys Cys Glu Cys Gly Ser Cys Val<br>575 580 585 | 1839 |
| tgt atc cag ccg ggc tcc tat ggg gac acc tgt gag aag tgc ccc acc<br>Cys Ile Gln Pro Gly Ser Tyr Gly Asp Thr Cys Glu Lys Cys Pro Thr<br>590 595 600 | 1887 |
| tgc cca gat gcc tgc acc ttt aag aaa gaa tgt gtg gag tgt aag aag<br>Cys Pro Asp Ala Cys Thr Phe Lys Lys Glu Cys Val Glu Cys Lys Lys<br>605 610 615 | 1935 |
| ttt gac cgg gga gcc cta cat gac gaa aat acc tgc aac cgt tac tgc<br>Phe Asp Arg Gly Ala Leu His Asp Glu Asn Thr Cys Asn Arg Tyr Cys<br>620 625 630 635 | 1983 |
| cgt gac gag att gag tca gtg aaa gag ctt aag gac act ggc aag gat<br>Arg Asp Glu Ile Glu Ser Val Lys Glu Leu Lys Asp Thr Gly Lys Asp<br>640 645 650 | 2031 |
| gca gtg aat tgt acc tat aag aat gag gat gac tgt gtc gtc aga ttc<br>Ala Val Asn Cys Thr Tyr Lys Asn Glu Asp Asp Cys Val Val Arg Phe<br>655 660 665 | 2079 |
| cag tac tat gaa gat tct agt gga aag tcc atc ctg tat gtg gta gaa<br>Gln Tyr Tyr Glu Asp Ser Ser Gly Lys Ser Ile Leu Tyr Val Val Glu<br>670 675 680 | 2127 |
| gag cca gag tgt ccc aag ggc cct gac atc ctg gtc gtc ctg ctc tca<br>Glu Pro Glu Cys Pro Lys Gly Pro Asp Ile Leu Val Val Leu Leu Ser<br>685 690 695 | 2175 |
| gtg atg ggg gcc att ctg ctc att ggc ctt gcc gcc ctg ctc atc tgg<br>Val Met Gly Ala Ile Leu Leu Ile Gly Leu Ala Ala Leu Leu Ile Trp<br>700 705 710 715 | 2223 |
| aaa ctc ctc atc acc atc cac gac cga aaa gaa ttc gct aaa ttt gag<br>Lys Leu Leu Ile Thr Ile His Asp Arg Lys Glu Phe Ala Lys Phe Glu<br>720 725 730 | 2271 |
| gaa gaa cgc gcc aga gca aaa tgg gac aca gcc aac aac cca ctg tat<br>Glu Glu Arg Ala Arg Ala Lys Trp Asp Thr Ala Asn Asn Pro Leu Tyr<br>735 740 745 | 2319 |
| aaa gag gcc acg tct acc ttc acc aat atc acg tac cgg ggc act<br>Lys Glu Ala Thr Ser Thr Phe Thr Asn Ile Thr Tyr Arg Gly Thr<br>750 755 760 | 2364 |
| taatgataag cagtcatcct cagatcatta tcagcctgtg ccaggattgc aggagtccct | 2424 |
| gccatcatgt ttacagagga cagtatttgt ggggagggat ttcggggctc agagtggggt | 2484 |
| aggttgggag aatgtcagta tgtggaagtg tgggtctgtg tgtgtgtatg tgggggtctg | 2544 |
| tgtgtttatg tgtgtgtgtt gtgtgtggga gtgtgtaatt taaaattgtg atgtgtcctg | 2604 |
| ataagctgag ctccttagcc tttgtcccag aatgcctcct gcagggattc ttcctgctta | 2664 |
| gcttgagggt gactatggag ctgagcaggt gttcttcatt acctcagtga aagccagct | 2724 |
| ttcctcatca ggccattgtc cctgaagaga agggcagggc tgaggcctct cattccagag | 2784 |
| gaagggacac caagccttgg ctctaccctg agttcataaa tttatggttc tcaggcctga | 2844 |
| ctctcagcag ctatggtagg aactgctggc ttggcagccc gggtcatctg tacctctgcc | 2904 |
| tcctttcccc tccctcaggc cgaaggagga gtcagggaga gctgaactat tagagctgcc | 2964 |
| tgtgcctttt gccatcccct caacccagct atggttctct cgcaagggaa gtccttgcaa | 3024 |
| gctaattctt tgacctgttg ggagtgagga tgtctgggcc actcagggt cattcatggc | 3084 |
| ctgggggatg taccagcatc tcccagttca taatcacaac ccttcaaaga tttgccttat | 3144 |
| tggcagctct actctggagg tttgtttaga agaagtgtgt caccccttagg ccagcaccat | 3204 |
| ctctttacct cctaattcca caccctcact gctgtagaca tttgctatga cctggggatg | 3264 |

```
tctctcatga ccaaatgctt ttcctcaaag ggagagagtg ctattgtaga gccagaggtc    3324
tggccctatg cttccggcct cctgtccctc atccatagca cctccacata cctggccctg    3384
agccttggtg tgctgtatcc atccatgggg ctgattgtat ttaccttcta cctcttggct    3444
gccttgtgaa ggaattattc ccatgagttg gctgggaata agtgccagga tggaatgatg    3504
ggtcagttgt atcagcacgt gtggcctgtt cttctatggg ttacaacctc atttaactca    3564
gtctttaatc tgagaggcca cagtgcaatt ttattttatt tttctcatga tgaggttttc    3624
ttaacttaaa agaacatgta tataaacatg cttgcattat atttgtaaat ttatgtgtat    3684
ggcaaagaag gagagcatag gaaaccacac agacttgggc agggtacaga cactcccact    3744
tggcatcatt cacagcaagt cactggccag tggctggatc tgtgaggggc tctctcatga    3804
tagaaggcta tggggataga tgtgtggaca cattggacct ttcctgagga agagggactg    3864
ttcttttgtc ccagaaaagc agtggctcca ttggtgttga catacatcca acattaaaag    3924 ccaccccaa atgcccaaga aaaaagaaa gacttatcaa catttgttcc atgagcagaa    3984
aactggagct ctggcctcag tgttacagct aaataatctt taattaaggc aagtcacttt    4044
cttcttctta aagctgtttc tagtttgaga atgatggga ttttagcagc cagtcttgaa    4104
ggtctctttc agtatcaaca ttctaagatg ctgggactta ctgtgtcatc aaatgtgcgg    4164
ttaagattct ctgggatatt gatactgttt gtgttttag ttgggagatc tgagagacct    4224
ggctttggca agagcagatg tcattccata tcacctttct caatgaaagt ctcattctat    4284
cctctctcca acccgttttt ccaacatttg ttaatagtta cgtctctcct gatgtagcac    4344
ttaagcttca tttagttatt atttctttct tcactttgca cacatttgca tccacatatt    4404
agggaaggaa taagtagctg caaactatct attcctgtat tattgtgtta acattgagat    4464
aaacc                                                                4469
```

<210> SEQ ID NO 6
<211> LENGTH: 762
<212> TYPE: PRT
<213> ORGANISM: Homo sapiens

<400> SEQUENCE: 6

```
Gly Pro Asn Ile Cys Thr Thr Arg Gly Val Ser Ser Cys Gln Gln Cys
1               5                   10                  15

Leu Ala Val Ser Pro Met Cys Ala Trp Cys Ser Asp Glu Ala Leu Pro
            20                  25                  30

Leu Gly Ser Pro Arg Cys Asp Leu Lys Glu Asn Leu Leu Lys Asp Asn
        35                  40                  45

Cys Ala Pro Glu Ser Ile Glu Phe Pro Val Ser Glu Ala Arg Val Leu
    50                  55                  60

Glu Asp Arg Pro Leu Ser Asp Lys Gly Ser Gly Asp Ser Ser Gln Val
65                  70                  75                  80

Thr Gln Val Ser Pro Gln Arg Ile Ala Leu Arg Leu Arg Pro Asp Asp
                85                  90                  95

Ser Lys Asn Phe Ser Ile Gln Val Arg Gln Val Glu Asp Tyr Pro Val
            100                 105                 110

Asp Ile Tyr Tyr Leu Met Asp Leu Ser Tyr Ser Met Lys Asp Asp Leu
        115                 120                 125

Trp Ser Ile Gln Asn Leu Gly Thr Lys Leu Ala Thr Gln Met Arg Lys
    130                 135                 140

Leu Thr Ser Asn Leu Arg Ile Gly Phe Gly Ala Phe Val Asp Lys Pro
145                 150                 155                 160
```

```
Val Ser Pro Tyr Met Tyr Ile Ser Pro Pro Glu Ala Leu Glu Asn Pro
                165                 170                 175

Cys Tyr Asp Met Lys Thr Thr Cys Leu Pro Met Phe Gly Tyr Lys His
            180                 185                 190

Val Leu Thr Leu Thr Asp Gln Val Thr Arg Phe Asn Glu Glu Val Lys
        195                 200                 205

Lys Gln Ser Val Ser Arg Asn Arg Asp Ala Pro Glu Gly Gly Phe Asp
    210                 215                 220

Ala Ile Met Gln Ala Thr Val Cys Asp Glu Lys Ile Gly Trp Arg Asn
225                 230                 235                 240

Asp Ala Ser His Leu Leu Val Phe Thr Thr Asp Ala Lys Thr His Ile
                245                 250                 255

Ala Leu Asp Gly Arg Leu Ala Gly Ile Val Gln Pro Asn Asp Gly Gln
            260                 265                 270

Cys His Val Gly Ser Asp Asn His Tyr Ser Ala Ser Thr Thr Met Asp
        275                 280                 285

Tyr Pro Ser Leu Gly Leu Met Thr Glu Lys Leu Ser Gln Lys Asn Ile
    290                 295                 300

Asn Leu Ile Phe Ala Val Thr Glu Asn Val Val Asn Leu Tyr Gln Asn
305                 310                 315                 320

Tyr Ser Glu Leu Ile Pro Gly Thr Thr Val Gly Val Leu Ser Met Asp
                325                 330                 335

Ser Ser Asn Val Leu Gln Leu Ile Val Asp Ala Tyr Gly Lys Ile Arg
            340                 345                 350

Ser Lys Val Glu Leu Glu Val Arg Asp Leu Pro Glu Glu Leu Ser Leu
        355                 360                 365

Ser Phe Asn Ala Thr Cys Leu Asn Asn Glu Val Ile Pro Gly Leu Lys
    370                 375                 380

Ser Cys Met Gly Leu Lys Ile Gly Asp Thr Val Ser Phe Ser Ile Glu
385                 390                 395                 400

Ala Lys Val Arg Gly Cys Pro Gln Glu Lys Glu Lys Ser Phe Thr Ile
                405                 410                 415

Lys Pro Val Gly Phe Lys Asp Ser Leu Ile Val Gln Val Thr Phe Asp
            420                 425                 430

Cys Asp Cys Ala Cys Gln Ala Gln Ala Glu Pro Asn Ser His Arg Cys
        435                 440                 445

Asn Asn Gly Asn Gly Thr Phe Glu Cys Gly Val Cys Arg Cys Gly Pro
    450                 455                 460

Gly Trp Leu Gly Ser Gln Cys Glu Cys Ser Glu Glu Asp Tyr Arg Pro
465                 470                 475                 480

Ser Gln Gln Asp Glu Cys Ser Pro Arg Glu Gly Gln Pro Val Cys Ser
                485                 490                 495

Gln Arg Gly Glu Cys Leu Cys Gly Gln Cys Val Cys His Ser Ser Asp
            500                 505                 510

Phe Gly Lys Ile Thr Gly Lys Tyr Cys Glu Cys Asp Asp Phe Ser Cys
        515                 520                 525

Val Arg Tyr Lys Gly Glu Met Cys Ser Gly His Gly Gln Cys Ser Cys
    530                 535                 540

Gly Asp Cys Leu Cys Asp Ser Asp Trp Thr Gly Tyr Tyr Cys Asn Cys
545                 550                 555                 560

Thr Thr Arg Thr Asp Thr Cys Met Ser Ser Asn Gly Leu Leu Cys Ser
                565                 570                 575
```

Gly Arg Gly Lys Cys Glu Cys Gly Ser Cys Val Cys Ile Gln Pro Gly
             580                 585                 590

Ser Tyr Gly Asp Thr Cys Glu Lys Cys Pro Thr Cys Pro Asp Ala Cys
         595                 600                 605

Thr Phe Lys Lys Glu Cys Val Glu Cys Lys Lys Phe Asp Arg Gly Ala
     610                 615                 620

Leu His Asp Glu Asn Thr Cys Asn Arg Tyr Cys Arg Asp Glu Ile Glu
625                 630                 635                 640

Ser Val Lys Glu Leu Lys Asp Thr Gly Lys Asp Ala Val Asn Cys Thr
                 645                 650                 655

Tyr Lys Asn Glu Asp Asp Cys Val Val Arg Phe Gln Tyr Tyr Glu Asp
             660                 665                 670

Ser Ser Gly Lys Ser Ile Leu Tyr Val Val Glu Glu Pro Glu Cys Pro
         675                 680                 685

Lys Gly Pro Asp Ile Leu Val Val Leu Leu Ser Val Met Gly Ala Ile
     690                 695                 700

Leu Leu Ile Gly Leu Ala Ala Leu Leu Ile Trp Lys Leu Leu Ile Thr
705                 710                 715                 720

Ile His Asp Arg Lys Glu Phe Ala Lys Phe Glu Glu Glu Arg Ala Arg
                 725                 730                 735

Ala Lys Trp Asp Thr Ala Asn Asn Pro Leu Tyr Lys Glu Ala Thr Ser
             740                 745                 750

Thr Phe Thr Asn Ile Thr Tyr Arg Gly Thr
         755                 760

<210> SEQ ID NO 7
<211> LENGTH: 191
<212> TYPE: DNA
<213> ORGANISM: Homo sapiens

<400> SEQUENCE: 7
cagagctgga gtgttaactg ggcccaactg tgtctaaata caatctttct ttccatccag     60
gtgagcttca gcattgaggc caaggtgcga ggctgttccc aggagaagga gaagtccttt    120
accataaagc ccgtgggctt caaggacagc ctgatcgtcc aggtcacctt tgattggact    180
gtgcctgcca g                                                         191

<210> SEQ ID NO 8
<211> LENGTH: 70
<212> TYPE: PRT
<213> ORGANISM: Homo sapiens

<400> SEQUENCE: 8

Trp Ala Gln Leu Cys Leu Asn Thr Ile Phe Leu Ser Ile Gln Val Ser
1               5                   10                  15

Phe Ser Ile Glu Ala Lys Val Arg Gly Cys Ser Gln Glu Lys Glu Lys
            20                  25                  30

Ser Phe Thr Ile Lys Pro Val Gly Phe Lys Asp Ser Leu Ile Val Gln
        35                  40                  45

Val Thr Phe Asp Cys Asp Cys Ala Cys Gln Ala Gln Ala Glu Pro Asn
    50                  55                  60

Ser His Arg Cys Asn Asn
65                  70

<210> SEQ ID NO 9

```
<211> LENGTH: 22
<212> TYPE: DNA
<213> ORGANISM: Artificial
<220> FEATURE:
<223> OTHER INFORMATION: primer

<400> SEQUENCE: 9
tccagagctg gagtgttaac tg                                              22

<210> SEQ ID NO 10
<211> LENGTH: 21
<212> TYPE: DNA
<213> ORGANISM: Artificial
<220> FEATURE:
<223> OTHER INFORMATION: primer

<400> SEQUENCE: 10
ctggcaggca cagtcacaat c                                               21

<210> SEQ ID NO 11
<211> LENGTH: 22
<212> TYPE: DNA
<213> ORGANISM: Artificial
<220> FEATURE:
<223> OTHER INFORMATION: primer

<400> SEQUENCE: 11
tccagagctg gagtgttaac tg                                              22

<210> SEQ ID NO 12
<211> LENGTH: 21
<212> TYPE: DNA
<213> ORGANISM: Artificial
<220> FEATURE:
<223> OTHER INFORMATION: primer

<400> SEQUENCE: 12
ctggcaggca cagtcacaat c                                               21

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
ccatccaggt gagcttcagc                                                 20

<210> SEQ ID NO 14
<211> LENGTH: 22
<212> TYPE: DNA
<213> ORGANISM: Artificial
<220> FEATURE:
<223> OTHER INFORMATION: primer

<400> SEQUENCE: 14
agtggttgca ggtatatgag gg                                              22

<210> SEQ ID NO 15
<211> LENGTH: 14
<212> TYPE: DNA
<213> ORGANISM: Artificial
<220> FEATURE:
<223> OTHER INFORMATION: probe

<400> SEQUENCE: 15
```

-continued

```
gctgtcccca ggag                                                              14

<210> SEQ ID NO 16
<211> LENGTH: 16
<212> TYPE: DNA
<213> ORGANISM: Artificial
<220> FEATURE:
<223> OTHER INFORMATION: probe

<400> SEQUENCE: 16
gaggctgtgc ccagga                                                            16

<210> SEQ ID NO 17
<211> LENGTH: 15
<212> TYPE: DNA
<213> ORGANISM: Artificial
<220> FEATURE:
<223> OTHER INFORMATION: probe

<400> SEQUENCE: 17
gaggctgttc ccagg                                                             15

<210> SEQ ID NO 18
<211> LENGTH: 19
<212> TYPE: DNA
<213> ORGANISM: Artificial
<220> FEATURE:
<223> OTHER INFORMATION: probe

<400> SEQUENCE: 18
tgaacctaat agccatcgc                                                         19

<210> SEQ ID NO 19
<211> LENGTH: 191
<212> TYPE: DNA
<213> ORGANISM: Homo sapiens

<400> SEQUENCE: 19
cagagctgga gtgttaactg ggcccaactg tgtctaaata caatctttct ttccatccag            60
gtgagcttca gcattgaggc caaggtgcga ggctgtcccc aggagaagga gaagtccttt           120
accataaagc ccgtgggctt caaggacagc ctgatcgtcc aggtcacctt tgattggact           180
gtgcctgcca g                                                               191

<210> SEQ ID NO 20
<211> LENGTH: 191
<212> TYPE: DNA
<213> ORGANISM: Homo sapiens

<400> SEQUENCE: 20
cagagctgga gtgttaactg ggcccaactg tgtctaaata caatctttct ttccatccag            60
gtgagcttca gcattgaggc caaggtgcga ggctgtgccc aggagaagga gaagtccttt           120
accataaagc ccgtgggctt caaggacagc ctgatcgtcc aggtcacctt tgattggact           180
gtgcctgcca g                                                               191

<210> SEQ ID NO 21
<211> LENGTH: 191
<212> TYPE: DNA
<213> ORGANISM: Homo sapiens

<400> SEQUENCE: 21
```

```
cagagctgga gtgttaactg ggcccaactg tgtctaaata caatctttct ttccatccag    60
gtgagcttca gcattgaggc caaggtgcga ggctgttccc aggagaagga gaagtccttt   120
accataaagc ccgtgggctt caaggacagc ctgatcgtcc aggtcacctt tgattggact   180
gtgcctgcca g                                                        191
```

<210> SEQ ID NO 22
<211> LENGTH: 70
<212> TYPE: PRT
<213> ORGANISM: Homo sapiens

<400> SEQUENCE: 22

Trp Ala Gln Leu Cys Leu Asn Thr Ile Phe Leu Ser Ile Gln Val Ser
1               5                   10                  15

Phe Ser Ile Glu Ala Lys Val Arg Gly Cys Pro Gln Glu Lys Glu Lys
            20                  25                  30

Ser Phe Thr Ile Lys Pro Val Gly Phe Lys Asp Ser Leu Ile Val Gln
        35                  40                  45

Val Thr Phe Asp Cys Asp Cys Ala Cys Gln Ala Gln Ala Glu Pro Asn
    50                  55                  60

Ser His Arg Cys Asn Asn
65                  70

<210> SEQ ID NO 23
<211> LENGTH: 70
<212> TYPE: PRT
<213> ORGANISM: Homo sapiens

<400> SEQUENCE: 23

Trp Ala Gln Leu Cys Leu Asn Thr Ile Phe Leu Ser Ile Gln Val Ser
1               5                   10                  15

Phe Ser Ile Glu Ala Lys Val Arg Gly Cys Ala Gln Glu Lys Glu Lys
            20                  25                  30

Ser Phe Thr Ile Lys Pro Val Gly Phe Lys Asp Ser Leu Ile Val Gln
        35                  40                  45

Val Thr Phe Asp Cys Asp Cys Ala Cys Gln Ala Gln Ala Glu Pro Asn
    50                  55                  60

Ser His Arg Cys Asn Asn
65                  70

<210> SEQ ID NO 24
<211> LENGTH: 70
<212> TYPE: PRT
<213> ORGANISM: Homo sapiens

<400> SEQUENCE: 24

Trp Ala Gln Leu Cys Leu Asn Thr Ile Phe Leu Ser Ile Gln Val Ser
1               5                   10                  15

Phe Ser Ile Glu Ala Lys Val Arg Gly Cys Ser Gln Glu Lys Glu Lys
            20                  25                  30

Ser Phe Thr Ile Lys Pro Val Gly Phe Lys Asp Ser Leu Ile Val Gln
        35                  40                  45

Val Thr Phe Asp Cys Asp Cys Ala Cys Gln Ala Gln Ala Glu Pro Asn
    50                  55                  60

Ser His Arg Cys Asn Asn
65                  70